US009649303B2

(12) United States Patent
Penn

(10) Patent No.: US 9,649,303 B2

(45) Date of Patent: May 16, 2017

(54) METHODS AND TREATMENT FOR ALLERGIES AND INFLAMMATION ASSOCIATED WITH GASTROINTESTINAL DISEASES

(71) Applicant: MASTCELL PHARMACEUTICALS, INC., Raleigh, NC (US)

(72) Inventor: Dennis Penn, Raleigh, NC (US)

(73) Assignee: MASTCELL PHARMACEUTICALS, INC., Raleigh, NC (US)

(*) Notice: Subject to any disclaimer, the term of this patent is extended or adjusted under 35 U.S.C. 154(b) by 0 days.

(21) Appl. No.: 14/247,056

(22) Filed: Apr. 7, 2014

(65) Prior Publication Data

US 2014/0302153 A1 Oct. 9, 2014

Related U.S. Application Data

(63) Continuation of application No. 12/953,340, filed on Nov. 23, 2010, now abandoned, which is a continuation-in-part of application No. PCT/US2009/003191, filed on May 22, 2009.

(60) Provisional application No. 61/055,964, filed on May 23, 2008.

(51) Int. Cl.

| | |
|---|---|
| ***A61K 39/35*** | (2006.01) |
| ***A61K 39/36*** | (2006.01) |
| ***A01N 65/00*** | (2009.01) |
| ***A61K 36/00*** | (2006.01) |
| ***A01N 57/00*** | (2006.01) |
| ***A61K 31/675*** | (2006.01) |
| ***A61K 31/4535*** | (2006.01) |
| ***A61K 31/381*** | (2006.01) |
| ***A61K 31/445*** | (2006.01) |
| ***A61K 45/06*** | (2006.01) |
| ***A61K 39/00*** | (2006.01) |

(52) U.S. Cl.

CPC ........ *A61K 31/4535* (2013.01); *A61K 31/381* (2013.01); *A61K 31/445* (2013.01); *A61K 39/0008* (2013.01); *A61K 39/35* (2013.01); *A61K 45/06* (2013.01)

(58) Field of Classification Search

None

See application file for complete search history.

(56) References Cited

U.S. PATENT DOCUMENTS

| | | | |
|---|---|---|---|
| 3,272,826 | A | 9/1966 | Jucker et al. |
| 3,491,103 | A | 1/1970 | Jucker, etal. |
| 3,682,930 | A | 8/1972 | Bourquin et al. |
| 4,831,042 | A | 5/1989 | Villani |
| 5,393,890 | A | 2/1995 | Svoii et al. |
| 5,399,360 | A | 3/1995 | Surer et al. |
| 5,648,355 | A | 7/1997 | Theoharides |
| 5,994,357 | A | 11/1999 | Theoharides |
| 6,207,683 | B1 | 3/2001 | Aberg et al. |
| 6,207,684 | B1 | 3/2001 | Aberg |
| 6,730,332 | B2 | 5/2004 | Agarwal et al. |
| 6,774,137 | B2 | 8/2004 | Adam et al. |
| 6,776,982 | B2 | 8/2004 | Kis et al. |
| 6,777,429 | B1 | 8/2004 | Adam et al. |
| 6,913,749 | B2 | 7/2005 | Hellman |
| 7,048,928 | B2 | 5/2006 | Loria et al. |
| 7,226,934 | B1 | 6/2007 | Aberg et al. |
| 7,927,600 | B2 * | 4/2011 | Loria et al. ................ 424/185.1 |
| 2001/0038843 | A1 | 11/2001 | Hellman |
| 2002/0165254 | A1 | 11/2002 | Kis et al. |
| 2003/0031663 | A1 | 2/2003 | Hellman |
| 2004/0076625 | A1 | 4/2004 | Hellman |
| 2004/0171613 | A1 | 9/2004 | Iwamura et al. |
| 2004/0253311 | A1 | 12/2004 | Berlin et al. |
| 2006/0128810 | A1 | 6/2006 | Narumiya |
| 2007/0003580 | A1 | 1/2007 | Loria et al. |
| 2010/0166804 | A1 | 7/2010 | Penn |
| 2011/0206659 | A1 | 8/2011 | Penn |

FOREIGN PATENT DOCUMENTS

| | | |
|---|---|---|
| EP | 1101492 | 7/1999 |
| EP | 1101496 | 7/1999 |
| EP | 0748217 | 8/2002 |

(Continued)

OTHER PUBLICATIONS

Gui et al. J. Gastronenterol. Hepatol. 13:980-989, 1998.*

Schoch et al. J. Ocular. Pharm. Therap. 19(1)75-81, 2003.*

Aceves, et al., "Relationships and Fibrosis in Eosinophilic Inflammation, Tissue Remodeling, and Fibrosis in Eosinophlic Esophagitis", Immunol. Allergy Clin. N. Am., vol. 29, (2009), pp. 197-211.

Alangari, A., et al., "Clinical Features and Anaphylaxis in Children with Cold Urticaria", Pediatrics, (2004), pp. e313-e317, vol. 113.

Ali, H., et al., "Anaphylatoxin C3a Receptors in Asthma", Respiratory Research, vol. 6, No. 19, (Feb. 21, 2005).

Allergy and Asthma Disease Management Center, Anaphylaxis, http://www.aaaai.org/aadmc/ate/cetegory.asp?cat=990, pp. 1-15, (2006).

Ann Allergy 2000, The Diagnosis and Management of Urticaria: A Practice Parameter—Part II: Chronic Urticaria/Angioedema, Ann. Allergy, vol. 85, pp. S521-S544, (2000).

Anonymous; "Anaphylaxis, the Most Dangerous Allergic Reaction"; www.nutramed.com/allergy/anaphylaxis/htm.; Environmed Research Inc.; first accessed May 2006.

(Continued)

*Primary Examiner* — Nora Rooney

(74) *Attorney, Agent, or Firm* — Hoxie & Associates LLC

(57) ABSTRACT

Methods of the prophylaxis of the development of allergy in a patient at risk of sensitization to an antigen(s) or allergen(s) due to impaired gastrointestinal functions include administering a mast cell inhibitor, e.g., ketotifen, e.g., ketotifen fumarate. Methods for prophylactically treating, reducing, delaying or controlling gastrointestinal disorders include administering a mast cell stabilizer, e.g., ketotifen to a patient in need thereof. Pharmaceutical preparation, composition for use in methods described, are also disclosed. Also disclosed are methods of prophylaxis or treating gastrointestinal and esophageal inflammation, and methods for the prophylaxis of the development of additional allergies to a newly introduced substance in a patient with a preexisting allergy. Such methods include delivery of a mast cell stabilizer, e.g., ketotifen. Oral and topical administration are contemplated within the scope of the methods.

12 Claims, No Drawings

(56) References Cited

FOREIGN PATENT DOCUMENTS

| | | |
|---|---|---|
| WO | WO 98/43640 | 10/1998 |
| WO | WO 00/06531 | 2/2000 |
| WO | WO 00/21512 | 4/2000 |
| WO | WO 00/45847 | 8/2000 |
| WO | WO 01/19367 | 3/2001 |
| WO | WO 01/39774 | 6/2001 |
| WO | WO 2005/120465 | 12/2005 |
| WO | WO 2005/120511 | 12/2005 |
| WO | WO 2009/142772 | 11/2009 |

OTHER PUBLICATIONS

Asero et al; "Does Sensitization to Foods in Adults Occur Always in the Gut?"; Int Arch Allergy Immunol; 154:6; pp. 6-14; 2011.
Beaven, "Histamine", The New England Journal of Medicine; pp. 30-36, (Jan. 1, 1976).
Bennett, M, and Ball, C. Anaphylaxis: Severe Anaphylaxis Was Rare, http:/Iwww.eboncall.ora/CATSn36.htm, 1999.
Bennett, M, and Ball, C. Anaphylaxis: Severe Episodes in Hospital Were Rare, http://www.eboncall.org/CAT5n26.htm_1999.
Berlin, et al., "A Prospective Randomized Case Controlled Pilot Study to Evaluate the Effect of Ketotifen on the Adverse Events Associated with Peanut Desensitization in Children with Peanut Allergies", POSTER (2012).
Boner, A., et al., The Efficacy of Ketotifen in a Controlled Double-Blind Food Challenge Study in Patients with Food Allergy, Annals of Allergy, 1996 pp. 61-64 vol. 57.
Bowman, et al., "Failure to Induce Oral Tolerance in Mice is Predictive of Dietary Allergenic Potency among Foods with Sensitizing Capacity", Toxicological Sciences, vol. 106, No. 2, pp. 435-443, (2008).
Bowman, et al., "Differences in Allergenic Potential of Food Extracts following Oral Exposure in Mice Reflect Differences in Digestibility; Potential Approaches to Safety Assessment", Toxicological Sciences, vol. 102, No. 1, pp. 100-109, (2008).
Brunner R., et al. Aluminum per se and in the anti-acid drug sucralafate promotes sensitization via the oral route, 2009 pp. 890-897 vol. 64; Epub Feb. 5, 2009 (Abstract).
Burks, Factoring PAF in Anaphylaxis, N. Engl. J. Med. vol. 358, No. 1, www.nejm.org, (Jan. 3, 2008).
Burks et al., "Double-blind Placebo-controlled Trial of Oral Cromolyn in Children with Atopic Dermatitis and Documented Food Hypersensitivity", J. Allergy Clin. Immunol., pp. 417-423, (Feb. 1988).
Casale et al., "Omalizumab Pretreatment Decreases Acute Reactions after Rush Immunotherapy for Ragweed-Induced Seasonal Allergic Rhinitis", J. Allergy Clin. Immunol. vol. 117, No. 1, pp. 134-140, (2005).
Chang, et al., "Anti-IgE as a Mast Cell-Stabilizing Therapeutic Agent", J. Allergy Clin. Immunol., pp. 1203-1212, (Jun. 2006).
Chiang, C.H., et al, Therapeutic Effect and Pharmacokinetics of Ketotifen Transdermal Delivery System, Drugs Dev. Ind. Pharm., (Mar. 1998), 24 (3): pp. 213-217. (Abstract).
Cianferoni, A., et al., Anaphylaxis: A 7-Year Follow-Up Survey of 46 Children, Ann. Allergy Asthma Immunol. 2004, pp. 464-468 vol. 92.
Clark, A.T., et al., Interpretation of Tests for Nut Allergy in One Thousand Patients, in Relation to Allergy or Tolerance Clin. Exp. Allergy, pp. 1041-1045, vol. 33. (2003).
Cook, E. B., et al., Mechanisms of Antihistamines and Mast Cell Stabilizers in Ocular Allergic Inflammation, Medicinal Chemistry Reviews—Online 2004 pp. 333-347, vol. 1.
Cox et al., "Allergen Immunotherapy: A Practice Parameter Third Update", J. Allergy Clin. Immunol. pp. 1-55, (2010).
Craps, L.P., Immunologic and Therapeutic Aspects of Ketotifen, Journal of Allergy and Clinical Immunology, 1985 pp. 389-393 vol. 76 Issue 2 Part 2.
Crump, V.S.A., Idiopathic Anaphylaxis: An Update, Auckland Allergy Clinic., http://www.allergyclinic.co.nz/guides/56.html, pp. 1-5 (2003).
Cryer, B., et al., Strategies for Preventing NSAID-Induced Ulcers: Patients at High Risk of NSAID-Induced Ulcers May Require Prophylactic or Curative Therapy, Kuwait Pharmacy, pp. 1-8 http://kuwaitpharmacy.com/article.aspx?id=43. (Jan. 23, 2005).
Dehlink et al., "The Role of the High-Affinity IgE Receptor, FcERI, in Eosinophilic Gastrointestinal Diseases", Immunol Allergy Clin. Am. vol. 29, pp. 159-170, (2009).
Delaney, J., The Effect of Ketotifen on Aspirin-Induced Asthmatic Reactions, Clinical Allergy, 1983, pp. 247-251 vol. 13.
De Luca, L., Protection Against Laryngotracheobronchial obstruction and anaphylaxis with ketotifen and DSCG, (disodiumchromglycate) in patients with food allergy, Pediatr. Med. Chir. Nov.-Dec. 1988; 10 (6): pp. 621-623. (Abstract).
Disorders with Type 1 Hypersensitivity Reactions The Merck Manual, pp. 1-19 (2008).
Eliakim, R., et al., Ketotifen—Old Drug, New Indication, Reduction of Gastric Mucosal Injury, Scand. J.Gastroenterol., pp. 202-204, vol. 28, (1993).
Ellul-Micallef et al., "Effect of Oral Sodium Cromoglycate and Ketotifen in Fish-Induced Bronchial Asthma", Thorax, vol. 38, pp. 527-530, (1983).
Enviromed Research, Inc., Anaphylaxis, http://nutramed.com/allergy/anaphylaxls.htm. Retrieved Mar. 16, 2010 pp. 1-6.
Feng, et al., "Mast Cells Play a Crucial Role in *Staphylococcus aureus* Peptidoglycan-Induced Diarrhea", The American Journal of Pathology, vol. 171, No. 2, pp. 537-547, (Aug. 2007).
Forbes et al., "IL-9- and Mast Cell-Mediated Intestinal Permeability Predisposes to Oral Antigen Hypersensitivity", Ther Journal of Experimental Medicine, pp. 1-17, (2008).
Furlan, J., et al., Preventive Effect of Ketotifen on Bronchoconstriction Induced by Food Allergens, Respiration, p. 16 vol. 46 (1984) (Supplement.).
Ganeshan, et al., "Impairing Oral Tolerance Promotes Allergy and Anaphylaxis: A New Murine Food Allergy Model", J. Allergy, Clin. Immunol. pp. 231-238, (Jan. 2009).
Gelfand et al; www.medscape.com; pp. 1-15; 2004.
Greiff et al; "Effect of a Dual CCR3 and $H_1$-antagonist on Symptoms and Eosinophilic Inflammation in Allergic Rhinitis"; Respiratory Research; 11:17; pp. 1-9; 2010.
Haeberli, G., et al., Elevated Basal Serum Tryptase and Hymenoptera Venom Allergy: Relation to Severity of Sting Reactions and to Safety and Efficacy of Venom Immunotherapy, Clin. Exp. Allergy, 2003, pp. 1216-1220 vol. 33.
Hasala et al., "c-Jun N-terminal Kinase Mediates Constitutive Human Eosinophil Apoptosis", Pulmonary Pharmacology & Therapeutics, pp. 1-156, (2006).
Heyman et al; "The Effect of Ketotifen on Nitric Oxide Synthase Activity"; British Journal of Pharmacology; 120; 1545-1551; 1997.
Holgate et al; "Consensus Group on New-Generation Antihistamines (CONGA): Present Status and Recommendations"; Clin. Exp. Allergy; 33; pp. 1305-1324; 2003.
Hosey et al; "Exercise-Induced Anaphylaxis and Urticaria"; American Family Physician, Oct. 2001; vol. 64, No. 9, pp. 1367-1374.
Hung, C.R., Importance of Histamine, Glutathione and Oxyradicals in Modulating Gastric Hemorrhagic Ulcer in Septic Rats Clinical and Experimental Pharmacology and Physiology, 2000 pp. 306-312 vol. 27.
Hung, C.R., Modulation of Gastric Hemorrhage and Ulceration by Oxidative Stress and Histamine Release in *Salmonella* Tvphimorium-Infected Rats. Inflammopharmacology. vol. 13 No. 1-3. pp. 235-248 (2005).
Inoue, K., et al., Enhancement of Skin Permeation of Ketotifen by Supersaturation Generated by Amorphous Form of the Drug, Journal of Controlled Release 2005 pp. 1-3.
Israel, I., et al., The Effect of Polymorphisms of the Adrenergic Receptor on the Response to Regular Use of Albuterol in Asthma, American Journal of Respiratory and Critical Care Medicine, pp. 75-80, vol. 162, (2000).
Ives, A.J. et al. Evidence-Based Diagnosis of Food Allergy. Current Pediatrics, pp. 357-364, vol. 12, (2002).

(56) References Cited

OTHER PUBLICATIONS

Jackson et al; "Intestinal Permeability in Patients with Eczema and Food Allergy"; The Lancet; pp. 1285-1286; Jun. 13, 1981.
Jiang et al., "Computational Analysis of the Relationship Between Allerginicity and Digestibility of Allergenic Proteins in Simulated Gastric Fluid", BMC Bioinformatics, vol. 8, No. 375, (2007).
Jönsson et al; "Mast Cells and Company"; Frontiers in Immunology; pp. 1-18; Feb. 20, 2012.
Kalia, N., et al., Mechanism and Control of Gastric Mucosal Injury and Bleeding, Mast Cell Stabilization Prevents Ethanol-induced Rat Gastric Mucosal Injury: Mechanisms of Protection, Journal of Gastroenterology and Hepatology, 2000, pp. 133-141 vol. 15.
Karmeli, F., et al., Ketotifen and Nitroxides Decrease Capsaicin-Augmented Ethanol-Induced Gastric Damage in Rats Digestive Diseases and Sciences 1995 pp. 1140-1146, vol. 40 No. 5.
Katzka, "Eosinophilic Esophagitis", (Abstract), Curr. Opinion Gastroenterol., vol. 4, pp. 429-432, (Jul. 2006).
Kawakubo, K., et al., Role of Gastric Mast Cells in the Regulation of Central TRH Analog-induced Hyperemia in Rats Peptides 2005 pp. 1580-1589 vol. 26.
Krause, R.S., Anaphylaxis, eMedicine (http://www.emedlclne.com/emergltoplc25.htm) Apr. 29, 2005, pp. 1-25.
Kumar, A., et al., Why do people die of Anaphylaxis?—A Clinical Review, Clinical and Developmental Immunology, 2005 pp. 281-287, vol. 12, Issue 4.
Lacy et al; "The Treatment of Irritable Bowel Syndrome"; Therapeutic Advances in Gastroenterology; 2(4); pp. 221-238; 2009.
Lehmann, "Inhibitors of Transient Lower Esophageal Sphincter Relaxations ("Reflux Inhibitors") in the Future Treatment of GERD".
Leung, D.Y.M., et al., Effect of Anti-IgE Therapy in Patients with Peanut Allergy, The New England Journal of Medicine 2003 pp. 986-993 vol. 348.
Lewis, S.A., et al., The Promiscuity of Immunoglobulin E binding to Peanut Allergens, as Determined by Western Blotting, Correlates with the Severity of Clinial Symptoms, Clinical and Experimental Allergy, Jun. 2005 pp. 767-773 vol. 35 Issue 6.
Lipozencic, J., et al., Life Threatening Severe Allergic Reactions: Urticaria, Angioedema, and Anaphylaxis, Clinics in Dermatology. 2005, PD. 193-PD. 205 vol. 23.
Lo, Y., et al., Food Specific Immunoglobulin E Among Children with Atopic Dermatitis: A Retrospective Study, J. Microblol. Immunol. Infect. 2005, pp. 335-342 vol. 38.
Lojek, et al.; "Modulation of metabolic activity of phagocytes by antihistamines", Interdisc. Toxicol., vol. 4(1), pp. 15-19, (2011).
Lowy, I., On Guinea Pigs, Dogs and Men: Anaphylaxis and the Study of Biological Individuality, 1902-1939, Studies in History and Philosophy of Biological and Biomedical Sciences 2003 pp. 399-423 vol. 34.
Mallon, D., Laboratory Tests in the Diagnosis of Allergic Diseases, ASCIA Member Services: Patient Information Bulletin, Feb. 2005, http://www.medeserv.com.au/asclalaerlinfobulletlns/Laboratory_Tests.htm., pp. 1-5.
Marshall, J.K., et al., Ketotifen Treatment of Active Colitis in Patients with 5-Aminosalicylate Intolerance, http://gastroresource.com/en/cases.htm 1998, pp. 1-4.
Martin, U, et al, Dissociation between the anti-anaphylactic and the anti-histaminic actions of ketotifen, Naunyn Schmiedebergs Arch Pharmacol Apr. 1981 316 (2): pp. 186-189. (Abstract).
Melillo, G., et al., Oral and Inhalation Provocation Tests for the Diagnosis of Aspirin-Induced Asthma, Allergy, 2001 pp. 899-911 vol. 56.
Menard et al; "Multiple Facets of Intestinal Permeability and epithelial Handling of Dietary Antigens"; Mucosal Immunology; pp. 1-13; Mar. 10, 2010.
Milgrom et al; "Treatment of Allergic Asthma with Monoclonal Anti-IgE Antibody"; The New England Journal of Medicine; pp. 1966-1973; Dec. 23, 1999.
Molkhou, P. et al. Food allergy and atopic dermatitis in children: treatment with oral sodium cromoglycate, Ann. Allergy 1981 47(3) pp. 173-175.
Molkhou, P. et al. Ketotifen in prevention of food allergy, Ann. Allergy 1987 59 (5 Pt 2) pp. 187-193 (Abstract submitted).
Molkhou, P. et al., Ketotifen Treatment of Atopic Dermatitis and Other Food Allergy Diseases, Allergy, vol. 44, pp. 117-123, Supp. 9, (1989).
Mullins R.J. Anaphylaxis: Risk Factors for Recurrence Clin. Exp. Allergy, 2003 pp. 1033-1040 vol. 33.
Nakamura et al., Platelet-Activating Factor (PAF) in Allergic Diseases: Inhibitory Effects of Anti-Allergic Drugs, Ketotifen and Three Kampo Medicines on PAF Production:, Lipids, vol. 26, No. 12, pp. 1297-1300, (1991).
Narendranathan, M., et al. Ketotifen in Prevention of Indomethacin-induced Gastropathy, Indian Journal of Gastroenterology. 1999 DD.76-DD.78 vol. 18.
National Institute of Allergy and Infectious Diseases, National Institutes of Health U.S. Department of Health and Human Services, Facts & Figures: Allergy Statistics, pp. 1-4, http://www.nlald.nlh.gov/factsheets/allergystat.htm_2006.
National Institute of Allergy and Infection Diseases (NIAID), Press Release "Protein Suppresses Allergic Response in Mice", (Nov. 18, 2007).
National Institute of Allergy and Infection Diseases, National Institutes of Health, "Report of the NIH Expert Panel of Food Allergy Research", (Mar. 13-14, 2006), pp. 1-21.
Neffen, H., et al., A Study of the Protective Effect of Ketotifen in Food Allergy, Allergologia Et Immunopathology 1980 pp. 97-104, vol. 8 No. 2.
Newman, et al., Epinephrine-resistant anaphylaxis in a patient taking propranolo hydrochloride, Ann, Allergy, Jul. 1981 47(1): pp. 35-37. (Abstract).
Nidus Information Services Inc., How are NSAID-Induced Ulcers Prevented and Treated?, http://www.nym.org/healthInfo/docs/019/doc19NsaldUlcer.htmI. , pp. 1-4 2001.
Okabe, S. et al, Effect of Ketotifen on Acute Gastric Lesions and Gastric Secretion in Rats, Jpn. J. Pharmacol. Jun. 1992 59(2): pp. 251-254.
Ottenhof M, et al, The Effect of Prednisolone and Ketotifen on the Antigen-Induced Bronchoconstriction and Mediator Release in Rat Isolated Lungs Br. J. Pharmacol. Nov. 1985 86(3): pp. 627-636.
Patriarca et al., "Oral Rush Desensitization in Peanut Allergy: A Case Report.", Digestive Disease and Sciences, vol. 51, No. 3, pp. 471-473, (2006).
Paschoal et al., "Food Allergy/Hypersensitivity: Antigenicity or Timing?", Immunobiology, vol. 214, pp. 269-278, (2009).
Patterson, R., et al., Malignant and Corticosteroid Dependent Idiopathic Anaphylaxis: Successful Responses to Ketotifen Annals of Allergy, Asthma and Immunology, 1997 pp. 138-144, vol. 79, No. 2.
Peters-Golden, M., et al., Cysteinyl Leukotriene Interactions with Other Mediators and with Glucocorticosteroids During Airway Inflammation, J. Allergy Clin. Immunol., Jan. 2003, pp. S37-S-48, vol. 111, No. 1.
Pfaar, et al., Aspirin Desensitization in Aspirin Intolerance: Update on Current Standards and Recent Improvements Allergy and Clinical Immunology, 2006 pp. 161-166 vol. 6 Lipincott Williams & Wilkins.
Pharmacia Diagnostics, ImmunoCAP Tryptase Is It Anaphylaxis?, Sweden Diagnostics (UK) Ltd., www.frca.co.ukldocumentsTryptase.pdf Retrieved Feb. 8, 2010.
Philpott et al., "Irritable Bowel Syndrome—An Inflammatory Disease Involving Mast Cells", Asia Pacific Allergy, vol. 1, pp. 36-42, (2011).
Pons, et al., "Towards Immunotherapy for Peanut Allergy", Curr. Opin. Allergy Clin. Immunol., (Dec. 2005) (Abstract).
Povoa, P., et al., A Case of Systemic Mastocytosis; Therapeutic Efficacy of Ketotifen, J.Intern Med., 1991, pp. 475-477 vol. 229.
Reeves, G., Assessment of Allergic Disease, HAPS, 1998, http://www.haps.nsw.gov.au/edrsrch/edInfo/aliergy.html pp. 1-6.
Remirez et al., "Eosinophilic Esophagitis", Allergologia et Immunopathologia, vol. 34, No. 2, pp. 79-81 (2006).

(56) References Cited

OTHER PUBLICATIONS

Resistentia Pharmaceuticals AB, Resistentia Pharmaceuticals Received Regulatory Approval to Begin Phase 1 Clinical Trial of its Novel Universal Allergy Immunotherapy, Press Release, (Feb. 6, 2006), Sweden.
Ring J. et al. History and Classification of Anaphylaxis Anaphylaxis 2004, pp. 6-24 Wiley.
Robinson, R. Allergy Tests, http://www.healthatoz/ency/allergy_tests_pr.jsp. pp. 1-4. Retrieved Feb. 6, 2006.
Robinson, R., Allergy Tests, Gale Encyclopedia of Medicine, http://www.healthatoz.com/healthatoz/Atoz/ency/allergy_tests_pr.jsp, pp. 1-4, (2002).
Romanski, B., et al., Protective Antianaphylactic Action of zaditen in Cases of Food Allergy, Respiration, 1981, p. 117 vol. 42, Supp. 1.
Rothenberg et al., "Eosinophilic Gastrointestinal Disorders (EGID)", J. Allergy Clin. Immunol., pp. 11-28, (Jan. 2004).
Rovati, G., et al., Cysteinyl Leukotrienes in the Regulation of B2-adrenoceptor function: An In Vitro Model of Asthma Respiratory Research 2006 vol. 7 No. 103.
Salvi et al., "Treatment of Allergic Asthma with Monoclonal Anti-IgE Antibody", The New England Journal of Medicine, p. 1292, (Apr. 27, 2000).
Sampson H. Anaphylaxis and Emergency Treatment, Pediatrics, vol. 111, pp. 1601-1608, (Jun. 2003).
Sampson, H.A., et al., Symposium on the Definition and Management of Anaphylaxis: Summary Report, J. Allergy Clin. Immunol. vol. 115, pp. 584-591, (2005).
Scholl et al., "Antiulcer Drugs Promote Oral Sensitization and Hypersensitivity to Hazelnut Allergens in BALB/c Mice and Humans", Am. J. Clin. Nutr., vol. 81, pp. 154-160, (2005).
Scholl et al. , "Anti-ulcer Treatment During Pregnancy Induces Food Allergy in Mouse Mothers and Th2-bias in their Offspring", FASEB Journal; vol. 21, pp. 1264-1270, (Apr. 2007).
Schuetze, G.E., et al., Bee Venom Allergy in Children: Long-Term Predictive Value of Standard Challenge Tests, Pediatric Allergy and Immunology, 2002, pp. 18-23, vol. 13, Blackwell Munksgaard, United Kingdom.
Schwartz, L.B., et al., Tryptase Levels as an Indicator of Mast-Cell Activation in Systemic Anaphylaxis and Mastocytosis The New England Journal of Medicine 1987 pp. 1622-1626 vol. 316 No. 26.
Sekardi, L., et al., Inhibition of Immunological Histamine Release from Guinea Pig Lungs and Other Organs by Mepyramine, Ketotifen,0 and Picumast In Vivo Arzneimittelforschung, 1989, pp. 1331-1335 vol. 39.
Serna et al., "Mast Cell Stabilizer Ketotifen [4-1(1-Methyl-4-piperidylidene)-4H-benzo[4,5]cyclohepta[1,2-b]thiophen-10(9H)-one Fumarate]Prevents Mucosal Mast Cell Hyperplasia and Intestinal Dysmotility in Experimental Trichinella spiralis Inflammation in the Rat", The Journal of Pharmacology and Experimental Therapeutics, vol. 319, No. 3, pp. 1104-1111, (2006).
Sheikh et al., "Oral Immunotherapy for the Treatment of Peanut Allergy: Systematic Review of Six Case Series Studies", Prim. Care Respir. J.; vol. 21, No. 1, pp. 41-49, (2012).
Sherman, "The Role of Mast Cells in Bacterial Enteritis", The American Journal of Pathology, vol. 171, No. 2, (Aug. 2007).
Sicherer et al; "Prevalence of Peanut and Tree Nut Allergy in the US Determined by a Random Digit Dial Telephone Survey"; J. Allergy Clin. Immunol., Apr. 1999; pp. 559-562.
Sicherer, S.H., et al., "Prevalence of Peanut and Tree Nut Allergy in the United States Determined by Means of a Random Digit Dial Telephone Survey: A 5-Year Follow-Up Study", J. Allergy Clin. Immunol., 2003, pp. 1203-1207 vol. 112.
Sicherer, S.H., et al., A Voluntary Registry for Peanut and Tree Nut Allergy: Characteristics of the First 5149 Registrants, J. Allergy Clin. Immunol, 2001, pp. 128-132, vol. 108.
Singh, "Modified-Release Solid Formulations for Colonic Delivery", Recent Patents on Drug Delivery & Formulation, vol. 1, pp. 53-63, (2007).
Smit, D., et al., Anaphylaxis Presentations to an Emergency Department in Hong Kong: Incidence and Predictors of Biphasic Reactions The Journal of Emergency Medicine 2005, pp. 381-388, vol. 28 No. 4.
Strohbach, The Effect of Various Non-Ulcer Pharmaceuticals, (text in German), Gasroenterol. J, vol. 51, No. 2, pp. 62-65, (1991).
Szczeklik, A., et al., Inhibition by Ketotifen of Idiosyncratic Reactions to Aspirin, Allergy, 1980, pp. 421-424, vol. 35.
Szczepanowska, A., et al, Ketotifen in the Treatment of Changes of the Upper Part of Digestive Tract in Allergic Children, Roczniki Akademii Medyecznej w Bialymstoku 1995 pp. 607-612 vol. 40, No. 3.
The Mastocytosis Society, Inc., Mastocytosis Mast Cell Activation Disorders, http://tmsforacure.org/patientinfo.shtml, pp. 1-4, (2004).
The Merck Manual, Disorders With Type 1 Hypersensitivity Reactions, www.merck.com/mrkshared/mmanuallsectlon12/chapter148/148b.isp, pp. 1-3 2006.
Thong, B., et al., Monitoring of IgE-Mediated Food Allergy in Childhood, Acta Paediatr, 2004, pp. 759-764, vol. 93.
Toit, G., et al., Optimizing the Diagnosis of Peanut and Tree Nut Allergy, Clin. Exp. Allergy, 2003, pp. 1019-1022, vol. 33.
Twarog, F.J., et al., Anaphylaxis Common in Children with Cold Urticaria, ResplratorRevlews.com, Jun. 2004 http://www.resplratoryrevlews.com/jun04/rr_jun04_anaphylaxis.html. pp. 1-3 vol. 9 No. 6.
Vadas et al., "Platelet-Activating Factor, PAF Acetylhydrolase, and Severe Anaphylaxis", The New England Journal of Medicine, vol. 358, No. 1, pp. 28-35, (2008).
Ventura, M., et al., Intestinal Permeability in Patients with Adverse Reactions to Food, Digestive and Liver Diseases' Official Journal of the Italian Society of Gastroenterology . . . , pp. 732-736, vol. 38, Issue 10, (2006).
Weisnagel, J., Peanut Allergy: Where Do We Stand?, Http://www.allerg.qc.ca/peanutallergy.htm, Dec. 1, 2005, pp. 1-130.
(Abstract) Wilhelms, Antagonism of Picumast and Ketotifen Against Histamine, Acetylcholine, L TC4, Slow-Reacting Substance of Anaphylaxis and Barium Chloride in the Guinea Pig Ileum Bioassay, Int., Arch. Appl. Immunol. 1987 pp. 544-546 vol. 82.
Woerly et al., "Inhibitory Effects on Ketotifen on Eotaxin-Dependent Activation of Eosinophils: Consequences for Allergic Eye Diseases", Allergy, vol. 58, pp. 397-406, (2003).
Wong, S., et al., Efficacy of Ketotifen in Corticosteroid-dependent Idiopathic anaphylaxis, Ann, Allergy, Sep. 1991; 67, (3): pp. 359-364. (Abstract).
Xolair, Xolair® Practice Management Handbook,: A Guide for Incorporating Xolair Into your practice, http://www.xolalr.com/pdffPractlceManagmentBlnder.pdf Retrieved Feb. 8, 2010.
Yan et al., "Eosinophilic Esophagitis" A Newly Established Cause of Dysphagia, World J. Gastroenterol., (vol. 12, No. 15, pp. 2328-2334, (Apr. 21, 2006).
Restriction Requirement issued Mar. 1, 2012 for U.S. Appl. No. 12/600,510.
Non-Final Office Action issued May 24, 2012 for U.S. Appl. No. 12/600,510.

* cited by examiner

METHODS AND TREATMENT FOR ALLERGIES AND INFLAMMATION ASSOCIATED WITH GASTROINTESTINAL DISEASES

REFERENCE TO RELATED APPLICATIONS

This application is a continuation application of U.S. Ser. No. 12/953,340 filed Nov. 23, 2010, which claims the benefit of PCT/US2009/003191, filed on May 22, 2009, and U.S. Provisional Application Ser. No. 61/055,964, filed May 23, 2008, the disclosures of each of which are hereby incorporated by reference in their entireties.

FIELD OF THE INVENTION

The present invention relates to methods for the prophylaxis of the development of allergy in a patient at risk of sensitization to an antigen(s) or allergen(s) due to impaired gastrointestinal functions comprising administering a mast cell inhibitor, e.g., ketotifen, e.g., ketotifen fumarate. The invention also provides methods for prophylactically treating, reducing, delaying or controlling symptoms of and inflammation associated with gastrointestinal disorders, e.g., due to exposure to allergen due to desensitization therapy and/or due to impaired gastrointestinal functions such as impaired gastrointestinal digestion and/or increased intestinal permeability, comprising administering a mast cell stabilizer, e.g., ketotifen. Also, methods of preventing or alleviating gastrointestinal and esophageal inflammation and tissue remodeling and fibrosis resulting therefrom, which comprise administering a mast cell stabilizer, e.g., ketotifen, by oral and topical administration, for example.

BACKGROUND

Over the past decade, concerns for the substantial increase in the prevalence of allergy have attracted much attention throughout the world. Food allergy affects as much as 25% of the population of Western countries and 8% of children under three years of age and approximately 2% in adults. The continued development and increasing number of cases of allergy, particularly to various food products, have raised serious concerns in the medical community. Recent studies have revealed an increase in hypersensitivity to allergen, particularly oral allergen, in patients with impaired gastrointestinal functions, particularly those with impaired gastrointestinal digestion and/or increased intestinal permeability or gastrointestinal barrier dysfunction, e.g., non-allergic inflammatory disease of the gastrointestinal tract, pharmacological agents that impair gastrointestinal digestion or concomitant gastrointestinal allergy. Allergy-associated gastrointestinal disease often gives rise to symptoms that can easily be confused with non-allergic gastrointestinal disease, e.g., vomiting, nausea, diarrhea, abdominal cramping, dyspepsia, gastro-esophageal reflux, heart burn, or difficulty in swallowing. Use of antacids to treat heart burn, for example, may promote the development of new allergy and delay the initiation of therapy appropriate for the underlying disease e.g., eosinophilic esophagitis. There is an urgent need for new treatments or prevention of allergy, particularly in those more susceptible to developing new allergy.

In allergic disease, platelet-activating factor has been recognized as an important mediator in the pathogenesis of allergic diseases, and Nakamura showed that ketotifen suppresses PAF production. Vadas et al. also showed that serum PAF levels were directly correlated with anaphylaxis.

Dehlink et al., have reported that gastrointestinal diseases such as primary eosinophilic gastrointestinal disorders (EGIDS) as being some form of allergic disorder. EGIDS include eosinophilic esophagitis, eosinophilic gastritis, eosinophilic gastroenteritis, and eosinophilic colitis. Patients with such diseases have concomitant IgE-mediated allergies to food and aeroallergen. Much data supporting pathogenic implications of IgE-mediated allergies for eosinophilic esophagitis has been demonstrated, but data for other EGID diseases having a role of IgE have been limited. Dehlink notes a role in the pathology of EGID diseases involving a high affinity receptor for IgE, Fc$\epsilon$RI, which has been implicated in IgE-mediated immune activation. Also, Fc$\epsilon$RI-mediated immune activation may be mediated by IgE-independent mechanism. This mechanism may be relevant for the pathology of EGIDS in patients lacking elevated serum IgE levels or symptoms attributable to specific allergens. In allergic diseases, platelet-activating factor has been implicated in the pathogenesis of allergic diseases such as bronchial asthma.

The esophagus is normally devoid of eosinophils, but in eosinophilic esophagitis, infiltration of eosinophils occurs, due to conditions such as food allergy, infection, gastro-esophageal reflux disease (GERD) or systemic eosinophilic conditions, for example. Yan et al., suggests treatment options to include specific food avoidance, topical corticosteroids, systemic corticosteroids, leukotriene inhibitors, and biologic treatment and thus suggest that the link between allergy and eosinophilic esophagitis. Remirez et al, further confirms this suggestion, by showing that a patient with eosinophilic esophagitis, had clinical relief upon elimination of diet including eggs upon treatment with ketotifen, a mast cell stabilizer, and montelukast, for example. However, easier administration means are needed. Other scientists such as Katzka et al., further conclude that eosinophilic esophagitis is an allergy-based disorder.

Woerly et al., notes that eosinophils are major effector cells in various allergic diseases and asthma, and suggests that drugs modulating various aspects of eosinophil function such as ketotifen play a role in the treatment of allergic eye diseases by inhibiting chemotaxis, thus suggesting a higher local concentration of drug to mucosa or submucosa may be beneficial.

Moreover, timing of food hypersensitivity may be critical. For example, Paschoal et al., noted that normal mice which eat peanuts are tolerant, but if they were immunized with peanut proteins prior to a challenge diet containing peanuts, the mice developed inflammation. Paschoal et al., also showed that introducing a new protein such as ovalbumin in mice immunized with peanut protein before commencing a 4 week peanut challenge diet induced tolerance, while introducing ovalbumin later in the challenge period induced greater protein antibody levels.

Also, certain substances may promote sensitization and inhibit tolerance of a previously tolerant compound. For example, Brunner et al., showed that co-administrating an anti-acid compound such as sucralfate, or aluminum, a component of sucralfate, with ovalbumin caused sensitization to previously tolerated ovalbumin, via elevation of the gastric pH and more so when administrated in conjunction with aluminum, a known adjuvant. The anti-acid compound and aluminum had shifted the immune response to a Th2 humoral immune response.

There needs to be improved methods of preventing unintended development of new sensitization to allergen, as well as treating and preventing symptoms of and inflammation in patients with allergy associated gastrointestinal and esophageal disease or conditions.

SUMMARY OF THE INVENTION

In the first aspect, the present invention provides a method (Method I) for the prophylaxis of the development of allergy in a patient at risk of sensitization to one or more antigen(s) or allergen(s) due to impaired gastrointestinal digestion and/or increased intestinal permeability if exposed to such allergen, comprising administering an effective amount of one or more mast cell stabilizer in free or pharmaceutically acceptable acid addition salt form.

In another embodiment, the invention provides Method I as follows:

1.1 Method I, wherein said patient suffers from increased intestinal permeability;

1.2 Method I or 1.1, wherein said patient suffers from one or more of the following: inflammatory bowel disease (IBD) (e.g., Crohn's disease, coeliac disease, colitis (e.g., ulcerative colitis, collagenous colitis, lymphocytic colitis, ischaemic colitis, diversion colitis, indeterminate colitis)), irritable bowel syndrome (IBS), allergy, gastritis, enteritis, esophagitis, and ulcers (gastric ulcer, duodenal ulcer, esophageal ulcer, stress-related ulcer, alcohol-related ulcer, drug-induced ulcers, e.g., NSAID-related ulcer, acetylsalicylic acid-induced ulcer, e.g., Aspirin-induced ulcer); concurrent gastrointestinal allergy to an unrelated allergen;

1.3 Method I or 1.1, wherein said patient is a recent heart or liver transplant patient taking tacrolimus;

1.4 Method I, wherein said patient suffers from impaired gastrointestinal digestion;

1.5 Method I or 1.4, wherein said patient suffers from one or more acid peptic diseases;

1.6 Method I, or any of methods 1.4-1.5, wherein said patient suffers from one or more disorders selected from the following: gastroesophageal reflux disease (GERD), dyspepsia, peptic ulcer (gastric ulcer, duodenal ulcer, esophageal ulcer, stress-related ulcer, alcohol-related ulcer, drug-induced ulcers, e.g., NSAID-related ulcer, acetylsalicylic acid-induced ulcer, e.g., Aspirin-induced ulcer), Zollinger-Ellison syndrome, Barrett's esophagus, gastrinomas, gastritis, eosinophilic gastritis, eosinophilic enteritis, and eosinophilic esophagitis;

1.7 Method I or any of methods 1.1-1.6, wherein said patient is a frequent user of one or more agents selected from a group consisting of proton pump inhibitors, antacids, histamine $H_2$-receptor antagonists, sucralfate, and $M_1$ muscarinic receptor antagonists;

1.8 Method I or any of methods 1.1-1.7, wherein said patient suffers from GERD;

1.9 Method I or any of methods 1.1-1.8, wherein said patient suffers from concomitant allergy associated gastrointestinal disease 1.10 Method I or any of methods 1.1-1.9, wherein said patient suffers from concomitant food allergy to additional allergens.

1.11 Method I or any of methods 1.1-1.8, wherein said patient suffers from one or more symptoms selected from a group consisting of diarrhea, bloating, loss of appetite, abdominal pain, constipation, nausea, vomiting, dyspepsia, dysphagia, regurgitation and esophageal reflux;

1.12 Method I or any of methods 1.1-1.11, wherein said patient is undergoing allergy desensitization (i.e., immunotherapy);

1.13 Method 1.12, further comprises administering, in conjunction with said mast cell stabilizer, one or more antigen(s) or allergen(s) to induce tolerance (i.e., desensitization therapy);

1.14 Method 1.13, wherein the allergen is administered orally, sublingually, subcutaneously, via inhalation, epicutaneously, intranasally, or parenterally (e.g., intravenously, intramuscularly, subcutaneously and intraperitoneally);

1.15 Method 1.13 or 1.14, wherein the allergen is administered orally;

1.16 Method 1.13 or 1.14, wherein the allergen is administered sublingually;

1.17 Method I or any of methods 1.1-1.16, wherein the antigen(s) or allergen(s) is administered to induce tolerance;

1.18 Method I or any of methods 1.1-1.16, wherein the antigen(s) or allergen(s) is ingested (e.g., during the normal course of food consumption, or any other means other than an act of administration);

1.19 Method I or any of methods 1.1-1.18, wherein the antigen(s) or allergen(s) (ingested or administered) is an alimentary canal sensitizing allergen;

1.20 Method I or any of methods 1.1-1.20, wherein the antigen(s) or allergen(s) is resistant to alimentary digestion;

1.21 Method I or any of methods 1.1-1.19, wherein the antigen(s) or allergen(s) is resistant to denaturation by gastric acid;

1.22 Method I or any of methods 1.1-1.18, wherein the antigen(s) or allergen(s) is susceptible to alimentary digestion;

1.23 Method I or any of methods 1.1-1.18 or 1.22, wherein the antigen(s) or allergen(s) is susceptible to denaturation by gastric acid;

1.24 Method I or any of methods 1.1-1.23, wherein the patient has experienced one or more episodes of allergic response(s) to the allergen(s) or antigen(s) ingested or administered;

1.25 Method I or any of methods 1.1-1.23, wherein the patient has not experienced any allergic response to the antigen(s) or allergen(s) ingested or administered;

1.26 Method I or any of methods 1.1-1.25, wherein the allergen(s) is selected from one or more allergens from seafood (e.g., fish, shellfish), tree nuts, hazelnuts, seeds, soy, peach, tomato, banana, strawberries, peanuts, celery, flour, rice, wheat, cow's milk, and eggs;

1.27 Method I or any of methods 1.1-1.26, wherein the allergen is from peanuts or hazelnuts;

1.28 Method I or any of methods 1.12-1.27, wherein the allergen is administered in increasing doses over a period of at least six weeks;

1.29 Method I or any of methods 1.12-1.28, wherein the allergen is administered at higher dosage or frequency than when the allergen is administered not in conjunction with the administration of a mast cell stabilizer;

1.30 Method I or any of methods 1.12-1.29, wherein the mast cell stabilizer is administered prior to, at the same time or after the administration of the allergen;

1.31 Method I or any of methods 1.12-1.30, wherein the mast cell stabilizer is administered prior to the commencement of each dose of allergen;

1.32 Method I or any of methods 1.12-1.31, wherein the mast cell stabilizer is administered up to two weeks prior to commencement of each does of allergen;

1.33 Method I or any of methods 1.12-1.32, wherein the mast cell stabilizer is administered up to 24 hours prior to commencement of each does of allergen;

1.34 Method I or any of methods 1.1-1.33, wherein the mast cell stabilizer is administered to prophylactically treat, control, delay, and/or normalize gastrointestinal disorders due to ingestion of the antigen(s) or allergen(s) (e.g., during the normal consumption of food);

1.35 Method I or any of methods 1.13-1.33, wherein the mast cell stabilizer is administered to prophylactically treat, control, delay, and/or normalize gastrointestinal disorders due to the administration of the allergen(s) or antigen(s) to induce tolerance (i.e., desensitization therapy);

1.36 Method I or any of methods 1.1-1.35, wherein the mast cell stabilizer is selected from a group consisting of: ketotifen, cromolyn, cromoglycate, nedocromil, bepotastine, ebastine, epinastine, azelastine, lodoxamide tromethamine, lodoxamide trometamol, pemirolast, olopatadine, ketotifen, norketotifen, 10-OH-norketotifen, 9-OH-norketotifen, 9,10-di-OH-norketotifen and those having the general formula:

I)

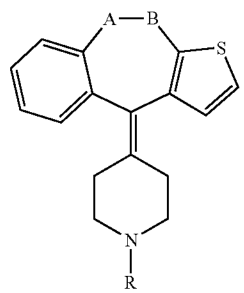

wherein:

a) -A-B- is a moiety having the formula:
   i) —CO—$CH_2$—
   ii) —$CH_2$—CO—
   iii) —$CH_2$—$CH_2$—
   iv) —CHOH—$CH_2$—
   v) —CHOH—CHOH—
   vi) —$CH_2$—CHOH—; or
   vii) —CO—CO—; and b) R is a hydroxyalkyl or a carboxyalkyloxyalkyl moiety;

II)

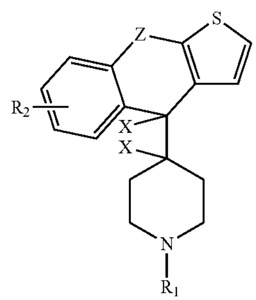

wherein:

a) —Z— is —$CH_2$—$CH_2$— or —CH═CH—;

b) $R_1$ is a H or $C_{1-4}$alkyl; and c) $R_2$ is H or halogen.

or III)

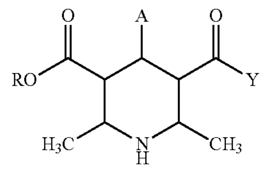

wherein:

a) A is

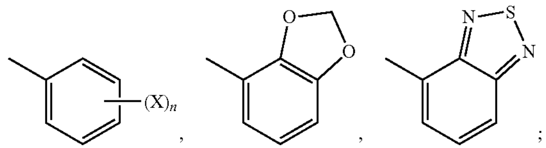

b) n is 1 or 2;
   when n is 1, X is H, halogen, $CF_3$, alkyne, —$S(O)_{n'}R$, OR or $NO_2$;
   when n is 2, X is H or halogen;

c) n' is 0, 1 or 2;

d) R is $C_{1-5}$(un)branched alkyl;

e) Y is $Z(C(R')(R'))_{n''}Z'$ or

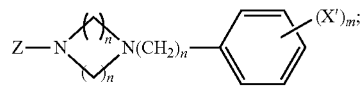

wherein:
   i) n" is 2-4;
   ii) m is 0, 1, 2, 3;
   iii) R' is H or R;
   iv) X' is H, halogen, $CF_3$, alkyne, —$S(O)_{n'}R$, OR or $NO_2$;
   v) Z is NH or O;
   vi) Z' is N(R')(R") or

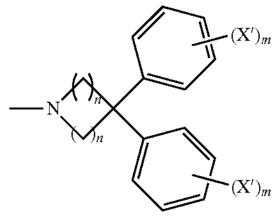

or R" is

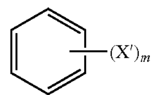

in free or pharmaceutically acceptable salt form;

1.37 Method I or any of methods 1.1-1.36, wherein said mast cell stabilizer is ketotifen in free or pharmaceutically acceptable salt form;

1.38 Method I or any of methods 1.1-1.37, wherein said salt is selected from a group consisting of hydrochloride, hydrobromide, hydrogen sulfate, phosphate, maleate, nitrate, besylate and fumarate;

1.39 Method I or any of methods 1.1-1.38, wherein said salt is fumarate salt;

1.40 Method I or any of methods 1.1-1.39, wherein the mast cell stabilizer is ketotifen fumarate;

1.41 Method I or any of methods 1.1-1.40, wherein ketotifen is administered in an oral dose of 0.01-0.1 mg/kg twice daily;

1.42 Method I or any of methods 1.1-1.41, wherein the patient receives an oral dose of 0.5-4 mg ketotifen twice daily;

1.43 Method I or any of methods 1.1-1.42, wherein the patient receives an oral dose of 0.5, 1 or 2 mg ketotifen twice daily;

1.44 Method I or any of methods 1.1-1.43, wherein the patient receives an oral dose of 1-6 mg of ketotifen once a day;

1.45 Method I or any of methods 1.1-1.44, wherein said mast cell stabilizer is administered in conjunction with one or more agents selected from a group consisting of proton pump inhibitors, antacids, histamine $H_2$-receptor antagonists, sucralfate, and $M_1$ muscarinic receptor antagonists, in free or pharmaceutically acceptable salt form;

1.46 Method 1.45, wherein said agent is a proton pump inhibitor in free or pharmaceutically acceptable salt form;

1.47 Method 1.45 or 1.46, wherein said proton pump inhibitor is selected from a group consisting of omeprazole, esomeprazole, pantoprazole, rabeprazole and lansoprazole in free or pharmaceutically acceptable salt form;

1.48 Method 1.45, wherein said agent is an antacid;

1.49 Method 1.45 or 1.48, wherein said antacid is selected from any of the following: aluminum hydroxide, magnesium carbonate, magnesium hydroxide, magnesium trisilicate, magnesium oxide, aluminum carbonate, calcium carbonate, sodium bicarbonate, hydrotalcite, bismuth subalicylate and magaldrate or any combination thereof (e.g., Gaviscon);

1.50 Method 1.45, wherein said agent is a histamine $H_2$-receptor antagonist in free or pharmaceutically acceptable salt form;

1.51 Method 1.45 or 1.50, wherein said histamine $H_2$-receptor antagonist is selected from a group consisting of cimetidine, ranitidine, famotidine, and nizatidine in free or pharmaceutically acceptable salt form;

1.52 Method 1.45, wherein said agent is sucralfate;

1.53 Any of the preceding methods, wherein said patient has a history of at least one episode of systemic anaphylactic reaction;

1.54 Any of the preceding methods wherein said patient undergoes expedited (RUSH) desensitization treatment;

1.55 Any of the preceding methods wherein said patient has a personal history of allergy and a family history of anaphylaxis;

1.56 Method I or any of methods 1.1-1.11, 1.18-1.27, 1.34, 1.36-1.56, wherein said patient is unwilling to undergo desensitization treatment;

1.57 Any of the preceding methods, wherein the mast cell stabilizer is enterically coated;

1.58 Method 1.57, wherein said enteric coat is selected from a group consisting of cellulose acetate phthalate, polyvinyl acetate phthalate, hydroxypropyl methylcellulose phthalate, acrylic copolymers (e.g., methacrylic acid-methacrylic acid ester copolymers), cellulose acetate trimethilate, carboxymethyl ethylcellulose and hydroxypropyl methyl-cellulose acetate succinate;

1.59 Any of the preceding methods wherein the effective amount of ketotifen is non-sedative (e.g., less than 2 mg, preferably less than 1 mg, more preferably less than 0.5 mg when administered to a patient three years or older, or less than 0.05 mg per kilogram of body weight, twice daily, wherein the patient is a child three years of age or younger.);

1.60 Method I or any of methods 1.1-1.59, further comprises administering at least one therapeutic agents selected from a group consisting of histamine-1 receptor antagonists, histamine-2 receptor antagonists, corticosteroids, PDE IV inhibitors, beta-adrenergic agonists, anticholinergic agents, epinephrine and IgE antagonists (including variant anti-IgE antibodies (non-human mammalian, chimeric, polyclonal and/or monoclonal antibodies (Mabs) and fragments thereof (e.g., proteolytic digestion or fusion protein products) and nucleotides or polypeptides encoding or containing IgE sequences or nucleotides or polypeptides that induce anti-IgE antibody production (e.g., anti-IgE immunogenic polypeptide as disclosed in U.S. Pat. No. 6,913,749, U.S. Pat. App. No. 2004/0076625A1 and 2003/0031663A1, the contents of each of which are herein incorporated by reference in their entirety), especially IgE antagonist and polypeptides capable of differential binding to Fc.epsilon.RI and Fc.epsilon.RII.); antagonist of cytokines, such as, for example, monoclonal antibody to TNF-alpha, soluble TNF-alpha receptor-Fc fusion protein, and/or IL-1 receptor; kinase inhibitors, e.g., inhibitors of spleen tyrosine kinase (syk), and inhibitors of kinase-activated pathways, e.g. inhibitors of STAT proteins;

1.61 Any of the preceding methods wherein said patient has diminished or inadequate response to $\beta_2$-adrenergic agonists;

1.62 Any of the preceding methods wherein said patient is resistant to epinephrine treatment;

1.63 Any of methods I or 1.1-1.62, wherein the patient is a regular user of long acting beta-agonists (LABAs);

1.64 Any of methods I or 1.1-1.62, wherein said patient is a regular user of $\beta_2$-adrenergic antagonist;

1.65 Any of the preceding methods, wherein the mast cell stabilizer is administered as a topical formulation or a drug delivery system.

1.66 Any of the preceding methods, wherein the drug delivery system is a liposomal carrier system.

1.67 Any of the preceding methods, wherein the topical formulation is selected from the group of a solution, a suspension, a gel, a bioadhesive, and an ointment.

In a preferred embodiment, the Invention provides Method I for the prophylaxis of the development of allergy in a patient at risk of sensitization to antigen(s) or allergen(s) due to impaired peptic diseases if exposed to such antigen(s) or allergen(s), comprising administering an effective amount of ketotifen fumarate to said patient.

In the second aspect, the invention provides a method (Method II) for prophylactically treating, controlling, delaying or normalizing gastrointestinal disorders comprising administering to a patient in need thereof an effective amount of one or more mast cell stabilizer in free or pharmaceutically acceptable salt form. Without being bound to any theory, it is believed that gastrointestinal disorders may be independent of the etiology of the diseases, but rather dependent of the alterations of the gastrointestinal barrier and the (in)ability of the body to digest or absorb allergen ingested during the course of food consumption, and moreover that (1) acid release in the stomach may be mediated in part by mast cell activation in the gut, and (2) mast cell activation in the gut may be exacerbated by reduced acid in the stomach, resulting in reduced degradation of peptide epitopes in the stomach. Therefore, in a further embodiment, the invention provides the following:

2.1 Method II, wherein said gastrointestinal disorder is a disorder associated with increased intestinal permeability;

2.2 Method II or 2.1, wherein said disorder is selected from one or more of the following: inflammatory bowel disease (IBD) (e.g., Crohn's disease, coeliac disease, colitis (e.g., ulcerative colitis, collagenous colitis, lymphocytic colitis, ischaemic colitis, diversion colitis, indeterminate colitis)), irritable bowel syndrome (IBS), allergy, gastritis, enteritis, esophagitis, and ulcers (gastric ulcer, duodenal ulcer, esophageal ulcer, stress-related ulcer, alcohol-related ulcer, drug-induced ulcers, e.g., NSAID-related ulcer, acetylsalicylic acid-induced ulcer, e.g., Aspirin-induced ulcer);

2.3 Method II or 2.1 or 2.2, wherein said gastrointestinal disorder is associated with impaired gastrointestinal digestion;

2.4 Method II or 2.1, 2.2 or 2.3, wherein said disorder is an acid peptic disease;

2.5 Method II or any of 2.1-2.4, said disorder is selected from the following: gastroesophageal reflux disease (GERD), dyspepsia, peptic ulcer (gastric ulcer, duodenal ulcer, esophageal ulcer, stress-related ulcer, alcohol-related ulcer, drug-induced ulcers, e.g., NSAID-related ulcer, acetylsalicylic acid-induced ulcer, e.g., Aspirin-induced ulcer), Zollinger-Ellison syndrome, Barrett's esophagus, gastrinomas, gastritis, eosinophilic gastritis, eosinophilic enteritis, and eosinophilic esophagitis;

2.6 Method II or any of 2.1-2.5, wherein said disorder is GERD;

2.7 Method II or any of 2.1-2.6, wherein said patient is a frequent user of one or more agents selected from a group consisting of proton pump inhibitors, antacids, histamine $H_2$-receptor antagonists, sucralfate, and $M_1$ muscarinic receptor antagonists;

2.8 Method II or any of 2.1-2.7, wherein said patient suffers from one or more symptoms selected from a group consisting of diarrhea, bloating, loss of appetite, abdominal pain, constipation, nausea, vomiting, dysphagia, dyspepsia, and esophageal reflux;

2.9 Method II or any of 2.1-2.8, wherein said patient is at risk of sensitization to antigen(s) or allergen(s) due to impaired gastrointestinal digestion and/or intestinal permeability;

2.10 Method II or any of 2.1-2.9, wherein said patient is undergoing allergy desensitization (i.e., immunotherapy);

2.11 Method 2.10, further comprises administering, in conjunction with said mast cell stabilizer, one or more antigen(s) or allergen(s) to induce tolerance (i.e., desensitization therapy);

2.12 Method II or any of 2.1-2.11, wherein the mast cell stabilizer is selected from a group consisting of: ketotifen, cromolyn, cromoglycate, nedocromil, bepotastine, ebastine, epinastine, azelastine, lodoxamide tromethamine, lodoxamide trometamol, pemirolast, olopatadine, ketotifen, norketotifen, 10-OH-norketotifen, 9-OH-norketotifen, 9,10-di-OH-norketotifen and those having the general formula:

I)

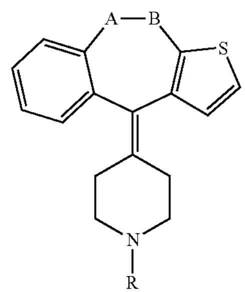

wherein:

a) -A-B- is a moiety having the formula:
  i) —CO—$CH_2$—
  ii) —$CH_2$—CO—
  iii) —$CH_2$—$CH_2$—
  iv) —CHOH—$CH_2$—
  v) —CHOH—CHOH—
  vi) —$CH_2$—CHOH—; or
  vii) —CO—CO—; and b) R is a hydroxyalkyl or a carboxyalkyloxyalkyl moiety;

II)

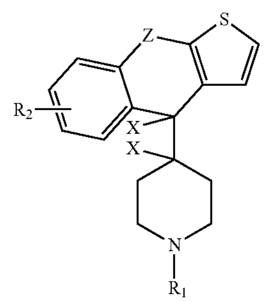

wherein:

a) —Z— is —$CH_2$—$CH_2$— or —CH═CH—;

b) $R_1$ is a H or $C_{1-4}$alkyl; and c) $R_2$ is H or halogen.

or III)

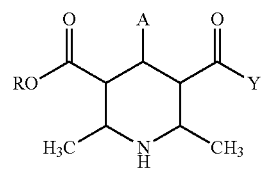

wherein:

a) A is

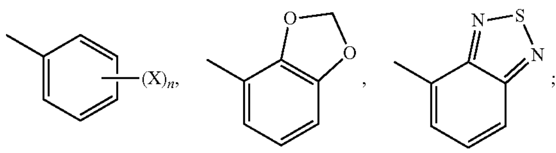

b) n is 1 or 2;

when n is 1, X is H, halogen, $CF_3$, alkyne, —S(O)$_{n'}$R, OR or $NO_2$;

when n is 2, X is H or halogen;

c) n' is 0, 1 or 2;

d) R is $C_{1-5}$(un)branched alkyl;

e) Y is Z(C(R')(R'))$_{n''}$Z' or

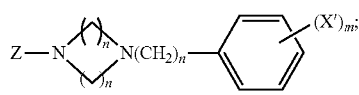

wherein:

i) n" is 2-4;

ii) m is 0, 1, 2, 3;

iii) R' is H or R;

iv) X' is H, halogen, $CF_3$, alkyne, —S(O)$_n$R, OR or $NO_2$;

v) Z is NH or O;

vi) Z' is N(R')(R") or

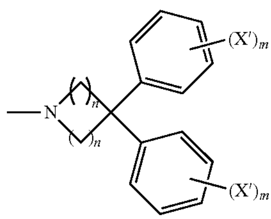

or R" is

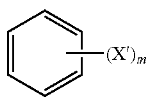

in free or pharmaceutically acceptable salt form;

2.13 Method II or any of methods 2.1-2.12, wherein the mast cell stabilizer is ketotifen in free or pharmaceutically acceptable salt form;

2.14 Method II any of methods 2.1-2.13, wherein the mast cell stabilizer is ketotifen fumarate;

2.15 Method II or any of methods 2.1-2.14, patient suffers from asthma or co-existing allergic disease (e.g., atopic dermatitis allergic rhinitis);

2.16 Method II or any of methods 2.1-2.15, wherein ketotifen is enterically coated;

2.17 Method 2.16, wherein the enteric coat is selected from a group consisting of cellulose acetate phthalate, polyvinyl acetate phthalate, hydroxypropyl methylcellulose phthalate, acrylic copolymers (e.g., methacrylic acid-methacrylic acid ester copolymers), cellulose acetate trimethilate, carboxymethyl ethylcellulose and hydroxypropyl methyl-cellulose acetate succinate;

2.18 Method 2.17, wherein enteric coated ketotifen is resistant against gastric acid digestion;

2.19 Method II or any of 2.1-2.18, wherein the effective amount of ketotifen is at a lower dosages than non-enteric coated ketotifen;

2.20 Method II or any of 2.1-2.19, the effective amount of ketotifen is a non-sedative amount (e.g., less than 2 mg, preferably less than 1 mg, more preferably less than 0.5 mg when administered to a patient three years or older, or less than 0.05 mg per kilogram of body weight, twice daily, e.g., wherein the patient is a child three years of age or younger.);

2.21 Any of the foregoing methods, wherein the effective amount of the mast cell stabilizer, e.g., ketotifen, is a non-sedative amount;

2.22 Any of the foregoing methods, wherein said mast cell stabilizer is administered in conjunction with an allergen to induce tolerance during desensitization therapy as described in, e.g., any of methods 1.13-1.55 or 1.57-1.64;

2.23 Any of the foregoing methods wherein said gastrointestinal disorder is NSAID-induced or ASA-induced, e.g., Aspirin-induced, gastrointestinal disorders (e.g., dyspepsia, e.g., GERD, bloating, belching, nausea);

2.24 Method 2.23, wherein said mast cell stabilizer is administered in conjunction with NSAID, e.g., Ibuprofen;

2.25 Method 2.23, wherein said mast cell stabilizer and said NSAID are enteric coated;

2.26 Method 2.23, wherein said mast cell stabilizer is administered in conjunction with ASA, e.g., aspirin;

2.27 Method 2.26, wherein said ASA is aspirin;

2.28 Method 2.26 or 2.27, wherein said aspirin is administered at a low dose, e.g., 81 mg;

2.29 Method 2.26, 2.27 or 2.28, wherein said aspirin is administered at 81 mg;

2.30 Any of methods 2.24-2.28, wherein said mast cell stabilizer and said ASA are enteric coated;

2.31 Any of the foregoing methods wherein said mast cell stabilizer is ketotifen in free or pharmaceutically acceptable salt form;

2.32 Any of the foregoing methods wherein said mast cell stabilizer is ketotifen fumarate.

2.33 Any of the preceding methods, wherein the mast cell stabilizer is administered as a topical formulation or a drug delivery system.

2.34 Any of the preceding methods, wherein the drug delivery system is a liposomal carrier system.

2.35 Any of the preceding methods, wherein the topical formulation is selected from the group of a solution, a suspension, a gel, a bioadhesive, and an ointment.

In the third aspect, the invention provides a combined pharmaceutical preparation (Pharmaceutical Preparation I) for simultaneous, separate or sequential use for the prophylaxis or treatment of gastrointestinal disorders comprising (i) one or more of a first agent(s) selected from a group consisting of proton pump inhibitors, antacids, histamine $H_2$-receptor antagonists, sucralfate, prostaglandin analogs, $M_1$ muscarinic receptor antagonists; and (ii) a mast cell stabilizer, in free or pharmaceutically acceptable salt form.

In another embodiment, the invention provides Pharmaceutical Preparation I as follows:

3.1 Pharmaceutical Preparation I, wherein said mast cell stabilizer is selected from a group consisting of cromolyn, cromoglycate, nedocromil, bepotastine, ebastine, epinastine, azelastine, lodoxamide tromethamine, lodoxamide trometamol, pemirolast, olopatadine, ketotifen, norketotifen, 10-OH-norketotifen, 9-OH-norketotifen, 9,10-di-OH-norketotifen and those having the general formula:

I)

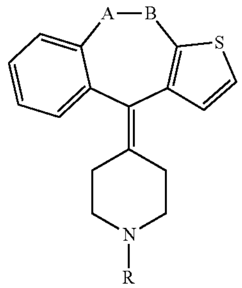

wherein:

a) -A-B- is a moiety having the formula:

i) —CO—$CH_2$— ii) —$CH_2$—CO— iii) —$CH_2$—$CH_2$— iv) —CHOH—$CH_2$— v) —CHOH—CHOH— vi) —$CH_2$—CHOH—; or vii) —CO—CO—; and b) R is a hydroxyalkyl or a carboxyalkyloxyalkyl moiety;

II)

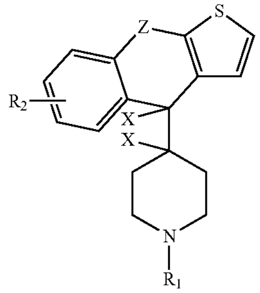

wherein:

a) —Z— is —$CH_2$—$CH_2$— or —CH═CH—;

b) $R_1$ is a H or $C_{1-4}$alkyl; and c) $R_2$ is H or halogen.

or III)

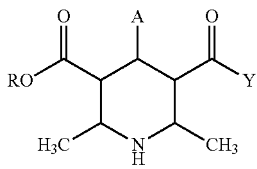

wherein:

a) A is

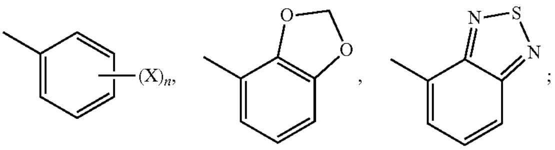

b) n is 1 or 2;

when n is 1, X is H, halogen, $CF_3$, alkyne, —$S(O)_{n'}R$, OR or $NO_2$;

when n is 2, X is H or halogen;

c) n' is 0, 1 or 2;

d) R is $C_{1-5}$(un)branched alkyl;

e) Y is $Z(C(R')(R'))_{n''}Z'$ or

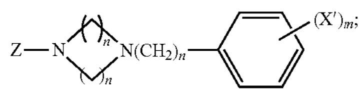

wherein:

i) n" is 2-4;

ii) m is 0, 1, 2, 3;

iii) R' is H or R;

iv) X' is H, halogen, $CF_3$, alkyne, —$S(O)_{n'}R$, OR or $NO_2$;

v) Z is NH or O;

vi) Z' is N(R')(R") or

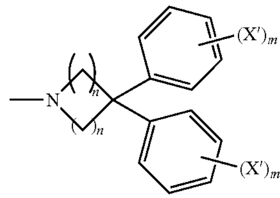

or R" is

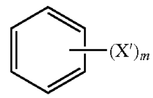

in free or pharmaceutically acceptable acid addition salt form;

3.2 Pharmaceutical Preparation 1 or 3.1, wherein said mast cell stabilizer is ketotifen in free or pharmaceutically acceptable salt form;

3.3 Pharmaceutical Preparation I or any of 3.1-3.2, wherein said salt is selected from a group consisting of hydrochloride, hydrobromide, hydrogen sulfate, phosphate, maleate, nitrate, besylate and fumarate;

3.4 Pharmaceutical Preparation I or any of 3.1-3.3 wherein said salt is fumarate salt;

3.5 Pharmaceutical Preparation I or any of 3.1-3.4, wherein said mast cell stabilizer is ketotifen fumarate;

3.6 Pharmaceutical Preparation I or any of 3.1-3.5, wherein said first agent comprises a proton pump inhibitor in free or pharmaceutically acceptable salt form;

3.7 Pharmaceutical Preparation I or any of 3.1-3.6, wherein said first agent is a proton pump inhibitor in free or pharmaceutically acceptable salt form;

3.8 Pharmaceutical Preparation I or any of 3.1-3.7, wherein said proton pump inhibitor is selected from a group consisting of omeprazole, esomeprazole, pantoprazole, rabeprazole and lansoprazole in free or pharmaceutically acceptable salt form;

3.9 Pharmaceutical Preparation I or any of 3.1-3.8, wherein said first agent comprises an antacid;

3.10 Pharmaceutical Preparation I or any of 3.1-3.9, wherein said first agent is an antacid;

3.11 Pharmaceutical Preparation I or any of 3.1-3.10, wherein said antacid is selected from any of the following: aluminum hydroxide, magnesium carbonate, magnesium hydroxide, magnesium trisilicate, magnesium oxide, aluminum carbonate, calcium carbonate, sodium bicarbonate, hydrotalcite, bismuth subalicylate and magaldrate or any combination thereof (e.g., Gaviscon);

3.12 Pharmaceutical Preparation I or any of 3.1-3.11, wherein said antacid is aluminum hydroxide and/or magnesium carbonate (e.g., Gaviscon);

3.13 Pharmaceutical Preparation I or any of 3.1-3.12, wherein said antacid is aluminum hydroxide and/or magnesium carbonate (e.g., Gaviscon) and the mast cell stabilizer is ketotifen in free or pharmaceutically acceptable salt form;

3.14 Pharmaceutical Preparation I or any of 3.1-3.11, wherein said first agent comprises an histamine $H_2$-receptor antagonist in free or pharmaceutically acceptable salt form;

3.15 Pharmaceutical Preparation I or any of 3.1-3.14, wherein said histamine $H_2$-receptor antagonist is selected from a group consisting of cimetidine, ranitidine, famotidine, and nizatidine in free or pharmaceutically acceptable salt form 3.16 Pharmaceutical Preparation I or any of 3.1-3.15, wherein said first agent comprises sucrafate;

3.17 Pharmaceutical Preparation I or any of 3.1-3.11, wherein said first agent comprises $M_1$ muscarinic receptor antagonists;

3.18 Any of the preceding pharmaceutical preparation for use in any of Method I, e.g., any of methods 1.1-1.64, or Method II, e.g., any of methods 2.1-2.22.

In a preferred embodiment, Pharmaceutical Preparation I comprises a proton pump inhibitor and ketotifen, in free or pharmaceutically acceptable salt form. In another preferred embodiment, Pharmaceutical Preparation I comprises an antacid and ketotifen, in free or pharmaceutically acceptable salt form. In yet another preferred embodiment, Pharmaceutical Preparation I comprises Gaviscon and ketotifen, in free or pharmaceutically acceptable salt form. Pharmaceutical Preparation I comprising ketotifen and antacid may increase topical resident time of ketotifen, thereby providing longer local effect.

In the fourth aspect, the invention provides a combined pharmaceutical preparation (Pharmaceutical Preparation II) for simultaneous, separate or sequential use for the prophylaxis or treatment of gastrointestinal disorders comprising (i) one or more of a first agent(s) selected from a non-steroidal anti-inflammatory drug (NSAID) or an acetylsalicylate (ASA) drug; and (ii) a mast cell stabilizer, in free or pharmaceutically acceptable salt form.

In a further embodiment, the invention provides Pharmaceutical Preparation II as follows:

4.1 Pharmaceutical Preparation II, wherein said first agent is non-steroidal anti-inflammatory drug;

4.2 Pharmaceutical Preparation II or 4.1, wherein said mast cell stabilizer and said NSAID are enteric coated;

4.3 Pharmaceutical Preparation II or 4.1 or 4.2, wherein said NSAID is ibuprofen or indomethacin;

4.4 Pharmaceutical Preparation II, wherein said wherein said first agent is ASA drug, e.g., aspirin;

4.5 Pharmaceutical Preparation II or 4.4, wherein said ASA drug is aspirin;

4.6 Pharmaceutical Preparation II or 4.4 or 4.5, wherein said aspirin is administered at a low dose, e.g., 81 mg;

4.7 Pharmaceutical Preparation II or any of 4.4-4.6, wherein said aspirin is administered at 81 mg;

4.8 Pharmaceutical Preparation II or any of 4.4-4.6, wherein said mast cell stabilizer and said ASA are enteric coated;

4.9 Any of the foregoing Pharmaceutical Preparation II wherein said mast cell stabilizer is described in any of the foregoing methods, e.g., in Method 1.36 or 2.12 or in Pharmaceutical preparation 3.1;

4.10 Any of the foregoing Pharmaceutical Preparation II wherein said mast cell stabilizer is ketotifen in free or pharmaceutically acceptable salt form;

4.11 Any of the foregoing Pharmaceutical Preparation II wherein said mast cell stabilizer is ketotifen fumarate.

In the fifth aspect, the invention provides an enteric coated mast cell stabilizer comprising (i) a mast cell stabilizer in free or pharmaceutically acceptable salt form; and (ii) an enteric coating.

In a further embodiment, the enteric coated mast cell stabilizer comprises the mast cell selected from a group consisting of ketotifen, cromolyn, cromoglycate, nedocromil, bepotastine, ebastine, epinastine, azelastine, lodoxamide tromethamine, lodoxamide trometamol, pemirolast, olopatadine, ketotifen, norketotifen, 10-OH-norketotifen, 9-OH-norketotifen, 9,10-di-OH-norketotifen and those having the general formula:

I)

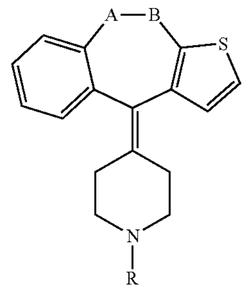

wherein:

a) -A-B- is a moiety having the formula:
  i) —CO—$CH_2$—
  ii) —$CH_2$—CO—
  iii) —$CH_2$—$CH_2$—
  iv) —CHOH—$CH_2$—
  v) —CHOH—CHOH—
  vi) —$CH_2$—CHOH—; or
  vii) —CO—CO—; and b) R is a hydroxyalkyl or a carboxyalkyloxyalkyl moiety;

II)

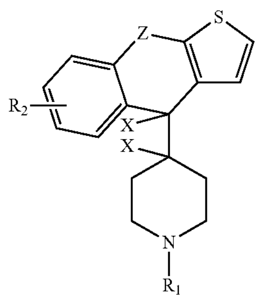

wherein:

a) —Z— is —$CH_2$—$CH_2$— or —CH═CH—;

b) $R_1$ is a H or $C_{1-4}$alkyl; and c) $R_2$ is H or halogen.

or III)

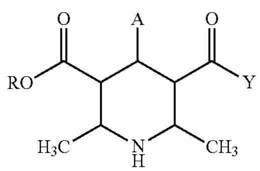

wherein:

a) A is

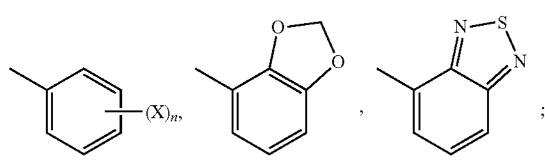

b) n is 1 or 2;

when n is 1, X is H, halogen, $CF_3$, alkyne, —S(O)$_{n'}$R, OR or $NO_2$;

when n is 2, X is H or halogen;

c) n' is 0, 1 or 2;

d) R is $C_{1-5}$(un)branched alkyl;

e) Y is Z(C(R')(R'))$_{n''}$Z' or

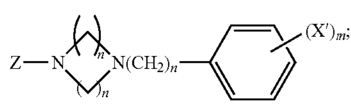

wherein:

i) n" is 2-4;

ii) m is 0, 1, 2, 3;

iii) R' is H or R;

iv) X' is H, halogen, $CF_3$, alkyne, —S(O)$_{n'}$R, OR or $NO_2$;

v) Z is NH or O;

vi) Z' is N(R')(R") or

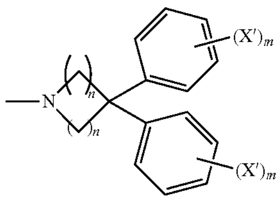

or R" is

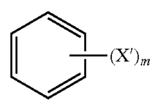

in free or pharmaceutically acceptable salt form.

In another embodiment, the enteric-coated mast cell stabilizer is an enteric coated ketotifen in free or pharmaceutically acceptable salt form. In still another embodiment, the enteric-coated mast cell stabilizer is an enteric coated ketotifen fumarate.

In still another embodiment, the enteric coated mast cell stabilizer further comprises an NSAID (e.g., ibuprofen or indomethacin) or an ASA drug (e.g., aspirin) in free or pharmaceutically acceptable salt form as described in hereinbefore, e.g., enteric coated Pharmaceutical Preparation II, e.g., 2.1-2.32.

In a further embodiment, the enteric coated mast cell stabilizer as disclosed hereinbefore comprises a polymeric enteric coating. Said polymeric enteric coating may be selected from a group consisting of cellulose acetate phthalate, polyvinyl acetate phthalate, hydroxypropyl methylcellulose phthalate, acrylic copolymers (e.g., methacrylic acid-methacrylic acid ester copolymers), cellulose acetate trimethilate, carboxymethyl ethylcellulose and hydroxypropyl methyl-cellulose acetate succinate.

In another embodiment, the enteric coated mast cell stabilizer as hereinbefore described may be used in any of the methods described in Method I, e.g., any of methods 1.1-1.64 or Method II, e.g., any of methods 2.1-2.32, Pharmaceutical Preparation I, e.g., 3.1-3.18, or Pharmaceutical Preparation II, e.g., 4.1-4.11. In a particular embodiment, the enteric coated mast cell stabilizer, e.g., enteric coated ketotifen, in free or pharmaceutically acceptable salt is resistant against acid digestion, e.g., against digestion by gastric acid, and therefore may be effective at a lower dosages than mast cell stabilizers that are not enteric coated.

In still another embodiment, the invention provides a pharmaceutical composition comprising: a mast cell stabilizer in free or pharmaceutically acceptable salt form as hereinbefore described in any of Method I, e.g., a any of methods 1.1-1.64, or Method II, e.g., any of methods 2.1-2.32; or 1) (i) one or more of a first agent(s) selected from a group consisting of proton pump inhibitors, antacids, histamine $H_2$-receptor antagonists, sucralfate, prostaglandin analogs, sucrafate, $M_1$ muscarinic receptor antagonists, and prokinetic agents; and (ii) a mast cell stabilizer, in free or pharmaceutically acceptable salt form as described in Pharmaceutical Preparation I, e.g., any of Preparation 3.1-3.18;

2) (i) one or more of a first agent(s) selected from a non-steroidal anti-inflammatory drug (NSAID) or an acetylsalicylate (ASA) drug; and (ii) a mast cell stabilizer, in free or pharmaceutically acceptable salt form;

3) an enteric coated mast cell stabilizer in free or pharmaceutically acceptable salt form as hereinbefore described, in admixture with a pharmaceutically acceptable diluent or carrier (Pharmaceutical Composition I). Pharmaceutical compositions of the Invention may be prepared using conventional diluents or excipients and techniques known in the galenic art. Thus oral dosage forms may include tablets, capsules, solutions, suspensions and the like. The Pharmaceutical Composition of the invention may be useful in any of Method I, e.g., any of methods 1.1-1.64, or Method II, e.g., any of methods 2.1-2.32.

The invention also provides use of:

1) a mast cell stabilizer in free or pharmaceutically acceptable salt form as hereinbefore described;

2) (i) a mast cell stabilizer and (ii) a proton pump inhibitor, antacid, histamine $H_2$-receptor antagonist, prostaglandin analog, sucrafate, $M_1$ muscarinic receptor antagonist, and prokinetic agent; in free or pharmaceutically acceptable salt form as described in Pharmaceutical Preparation I, e.g., any of Preparation 3.1-3.18;

3) an enteric coated mast cell stabilizer in free or pharmaceutically acceptable salt form as hereinbefore described; or 4) Pharmaceutical Composition I as described hereinbefore, in the manufacture of a medicament for the treatment of any of Method I, e.g., any of methods 1.1-1.64, or Method II, e.g., any of methods 2.1-2.32 or Pharmaceutical Preparation I, e.g., 3.1-3.18.

In one example, (Method III) comprises a method of prophylaxis and treating gastric and esophageal inflammation in a patient, in order to reduce signs and symptoms of inflammation, or to enhance repair of tissue and inhibit fibrosis, comprising:

administering a mast cell stabilizer as a topical formulation or as a drug delivery system. In further embodiments, Method III is provided as follows:

5.2 Method III, wherein the drug delivery system is a liposomal carrier.

5.3 Method III, wherein the step of administering administers the topical formulation selected from the group of a solution, a suspension, a gel, a bioadhesive and an ointment.

5.4 Method III, wherein the step of administering the topical formulation includes administering the mast cell stabilizer as a gel.

5.4 Method III, wherein the step of administering the topical formulation includes administering the mast cell stabilizer as a viscous gel and using at least one excipient.

5.5 Method III, or 5.4, wherein the topical formulation has a surface tension and a viscosity equivalent to that of a solution prepared by adding about sodium carboxymethylcellulose in a concentration of a range of 0.5% to 10%, wherein the low surface tension provides for an even film and allows for prolonged contact.

5.6 Method III, or 5.5, wherein the at least one excipient comprises a material adapted to float on gastrointestinal fluids contained in the stomach such that a carrier is located in a more proximate location to the gastric mucosa than the gastrointestinal fluids and the carrier is adapted to deliver a local anesthetic to the gastric mucosa such that a higher local concentration of the mast cell stabilizer is delivered to the stomach and lower esophagus.

5.7 Method III, or any of the previous embodiments, wherein the mast cell stabilizer is selected from a group consisting of: ketotifen, cromolyn, cromoglycate, nedocromil, bepotastine, ebastine, epinastine, azelastine, lodoxamide tromethamine, lodoxamide trometamol, pemirolast, olopatadine, ketotifen, norketotifen, 10-OH-norketotifen, 9-OH-norketotifen, 9,10-di-OH-norketotifen and those having the general formula:

I)

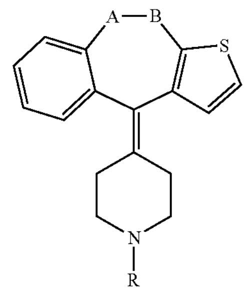

wherein:

a) -A-B- is a moiety having the formula:

i) —CO—$CH_2$— ii) —$CH_2$—CO— iii) —$CH_2$—$CH_2$— iv) —CHOH—$CH_2$— v) —CHOH—CHOH— vi) —$CH_2$—CHOH—; or vii) —CO—CO—; and b) R is a hydroxyalkyl or a carboxyalkyloxyalkyl moiety;

II)

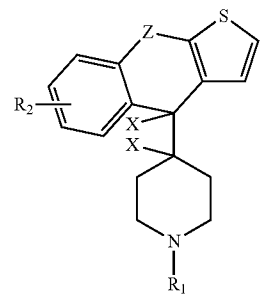

wherein:

a) —Z— is —$CH_2$—$CH_2$— or —CH═CH—;

b) $R_1$ is a H or $C_{1-4}$alkyl; and c) $R_2$ is H or halogen.

or III)

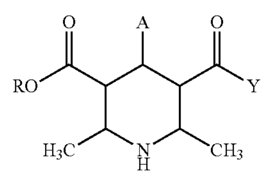

wherein:

a) A is

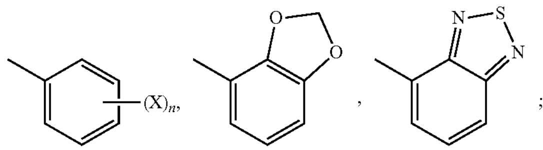

b) n is 1 or 2;

when n is 1, X is H, halogen, $CF_3$, alkyne, —$S(O)_{n'}R$, OR or $NO_2$;

when n is 2, X is H or halogen;

c) n' is 0, 1 or 2;

d) R is $C_{1-5}$(un)branched alkyl;

e) Y is $Z(C(R')(R'))_{n''}Z'$ or

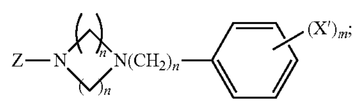

wherein:

i) n" is 2-4;

ii) m is 0, 1, 2, 3;

iii) R' is H or R;

iv) X' is H, halogen, $CF_3$, alkyne, —$S(O)_{n'}R$, OR or $NO_2$;

v) Z is NH or O;

vi) Z' is N(R')(R") or

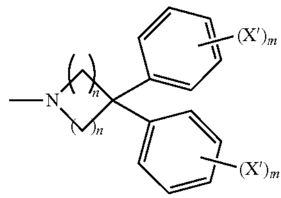

or R" is

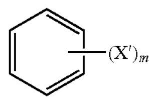

in free or pharmaceutically acceptable acid addition salt form.

5.8, Method III or any of the preceding embodiments, wherein the step of administering enhances repair of the tissue that is epithelial tissue.

5.9, Method III or any of the preceding embodiments, wherein the step of administering enhances the repair of tissue that is mesothelial tissue.

5.10, Method III or any of the preceding embodiments, wherein the step of administering includes using at least one excipient and administering the mast cell stabilizer as a viscous gel.

5.11 Method III or any of the preceding embodiments, wherein the step of administering includes combining the mast cell stabilizer with a corticosteroid.

5.12 Method III or any of the preceding embodiments, wherein the step of administering optionally includes combining the mast cell stabilizer with a corticosteroid, or substituting the mast cell stabilizer with the corticosteroid.

5.13 Method III or any of the preceding embodiments, wherein the step of administering allows for an elevated local concentration of the mast cell stabilizer in a targeted tissue.

5.14 Method III or any of the preceding embodiments, wherein the mast cell stabilizer is ketotifen in free or pharmaceutically acceptable salt form.

5.15 Method III, or any of the preceding embodiments, wherein the mast cell stabilizer is ketotifen fumarate.

5.16 Method III, or any of the preceding embodiments, wherein the patient suffers from one or more of the following: inflammatory bowel disease, irritable bowel syndrome (IBS), allergy, gastritis, esophagitis, and ulcers.

5.16 Method III, or any of the preceding embodiments, wherein the patient suffers from impaired gastric disease, or suffers from one or more peptic acid diseases.

5.17 Method III, or any of the preceding embodiments, wherein the patient suffers from one or more disorders selected from the following: gastroesophageal reflux disease, dyspepsia, heartburn, dysphagia, peptic ulcer, Zollinger-Ellison syndrome, Barrett's esophagus, gastrinomas, gastritis, eosinophilic gastritis, eosinophilic enteritis, and eosinophilic esophagitis.

In another aspect, Method IV, provides a method for the prophylaxis of the development of additional allergies to a newly introduced substance in a patient with a preexisting allergy: comprising: co-administering a mast cell stabilizer as a topical formulation or as a drug delivery system with the newly introduced substance. For example, the newly introduced substance may be introduced by administration or by exposure.

6.1 Method IV, wherein the drug delivery system is a liposomal carrier.

6.2 Method IV, wherein the step of administering administers the topical formulation selected from the group of a solution, a suspension, a gel, a bioadhesive, and an ointment.

6.3 Method IV, or 6.2, wherein the step of administering the topical formulation includes administering the mast cell stabilizer as a gel.

6.4 Method IV or any of the preceding embodiments, wherein the mast cell stabilizer is selected from a group consisting of: ketotifen, cromolyn, cromoglycate, nedocromil, bepotastine, ebastine, epinastine, azelastine, lodoxamide tromethamine, lodoxamide trometamol, pemirolast, olopatadine, ketotifen, norketotifen, 10-OH-norketotifen, 9-OH-norketotifen, 9,10-di-OH-norketotifen and those having the general formula:

I)

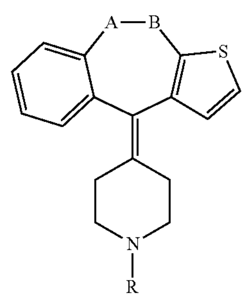

wherein:

c) -A-B- is a moiety having the formula:

viii) —CO—$CH_2$— ix) —$CH_2$—CO— x) —$CH_2$—$CH_2$— xi) —CHOH—$CH_2$— xii) —CHOH—CHOH— xiii) —$CH_2$—CHOH—; or xiv) —CO—CO—; and d) R is a hydroxyalkyl or a carboxyalkyloxyalkyl moiety;

II)

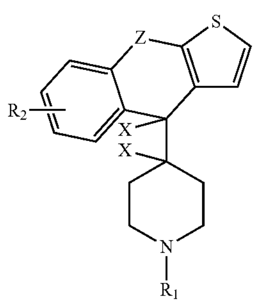

wherein:

d) —Z— is —$CH_2$—$CH_2$— or —CH═CH—;

e) $R_1$ is a H or $C_{1-4}$alkyl; and f) $R_2$ is H or halogen.

or III)

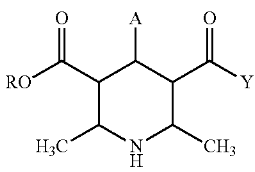

wherein:

f) A is

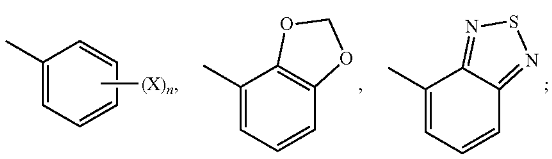

g) n is 1 or 2;

when n is 1, X is H, halogen, $CF_3$, alkyne, —$S(O)_n$R, OR or $NO_2$;

when n is 2, X is H or halogen;

h) n' is 0, 1 or 2;

i) R is $C_{1-5}$(un)branched alkyl;

j) Y is $Z(C(R')(R'))_{n''}Z'$ or

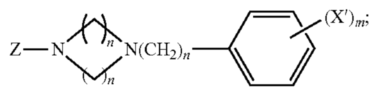

wherein:

vii) n" is 2-4;

viii) m is 0, 1, 2, 3;

ix) R' is H or R;

x) X' is H, halogen, $CF_3$, alkyne, —$S(O)_n$R, OR or $NO_2$;

xi) Z is NH or O;

xii) Z' is N(R')(R") or

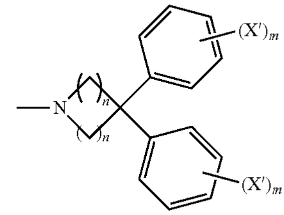

or R" is

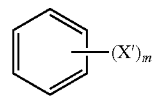

in free or pharmaceutically acceptable acid addition salt form.

6.5 Method IV, or any of the preceding embodiments, wherein the mast cell stabilizer is ketotifen in free or pharmaceutically acceptable salt form.

6.6 Method IV, or any of the preceding embodiments, wherein the mast cell stabilizer is ketotifen fumarate.

6.7 Method IV, or any of the preceding embodiments, wherein the newly introduced substance is selected from one or more allergen(s) in fish, shellfish, tree nuts, hazelnuts, seeds, soy, milk, peach, tomato, banana, strawberries, peanuts, celery, flour, rice, wheat, and eggs.

6.7 Method IV, or any of the preceding embodiments, wherein the allergen is peanuts or hazelnuts.

6.8 Method IV, or any of the preceding embodiments, wherein the patient suffers from one or more of the following: inflammatory bowel disease, irritable bowel syndrome (IBS), allergy, gastritis, esophagitis, and ulcers.

6.9 Method IV, or any of the preceding embodiments, wherein the patient suffers from impaired gastric disease, or suffers from one or more peptic acid diseases.

6.10 Method IV, or any of the preceding embodiments, wherein the patient suffers from one or more disorders selected from the following: gastroesophageal reflux disease, dyspepsia, heart burn, dysphagia, peptic ulcer, Zollinger-Ellison syndrome, Barrett's esophagus, gastrinomas, gastritis, eosinophilic gastritis, eosinophilic enteritis, and eosinophilic esophagitis.

The topical formulation including the mast cell stabilizer may prevent sensitization to a newly introduced substance in a patient with a preexisting gastrointestinal allergy, when the formulation is co-administered. Alternatively, a drug delivery system may be used. For example, a liposomal carrier may be used to deliver an effective amount of a mast cell stabilizer. Drug delivery systems are known in the art. Examples of drug delivery system include systems disclosed in U.S. Pat. No. 7,534,448.

The term "co-administering" include administering a mast cell stabilizer concurrently or sequentially, i.e., administering the mast cell stabilizer before administering the newly introduced substance or administering the mast cell stabilizer after administering the newly introduced substance.

It is also known that certain substances may promote sensitization and inhibit tolerance of a previously tolerant compound. While not bound by theory, the use of a mast cell stabilizer, that is co-administered with a sensitization-promoting agent and the normally tolerated allergen, may prevent sensitization to an allergen. For example, one may be tolerant to a peanut diet, but may be sensitized to peanuts when immunized first with a peanut protein before after eating a diet rich in peanuts. Thus, in one example, co-administering a mast-cell stabilizer with a sensitization-promoting agent, such as a peanut protein, may prevent the sensitization that may occur.

For example, it was known that co-administrating an anti-acid compound such as sucralfate, or aluminum, a component of sucralfate, with ovalbumin caused sensitization to previously tolerated ovalbumin, via elevation of the gastric pH. Thus, co-administering a mast cell stabilizer with sucralfate, may prevent sensitization that may occur.

The term "co-administering" include administering a mast cell stabilizer concurrently or sequentially, i.e., administering the mast cell stabilizer before administering the sensitization-promoting agent, or the newly introduced allergen or both or administering the mast cell stabilizer after administering the sensitization-promoting agent or allergen or both. For example, one may co-administer the topical formulation or the drug delivery system with the newly introduced allergen and the sensitization-promoting agent to prevent sensitization. Alternatively, one may co-administer the topical formulation or the drug delivery system with sensitization-promoting agent alone. Such methods of treatment are also contemplated within the scope of Method I.

Any sensitization-promoting agent may be used. For example, the sensitization-promoting agent may be a peanut protein, or any other nut protein, such as a Brazil nut protein. The sensitization-promoting agent may be an anti-acid drug. For example, one preferred drug is sucralfate, which contains aluminum, which is known to promote the Th2 response. Other anti-ulcer or anti-gastritis medications include for example, omeprazole, cimetidine, ranitidine, lansoprazole, pantoprazole, famotidine, or nizatidine, or antacids such as magnesium hydroxide, aluminum hydroxide, sodium carbonate, sodium hydrogen carbonate, simethicone or aluminum magnesium hydroxide. Other anti-acid drugs known in the art may be also be used.

DETAILED DESCRIPTION OF THE INVENTION

The examples and drawings provided in the detailed description are merely examples, which should not be used to limit the scope of the claims in any claim construction or interpretation.

In one embodiment, the invention encompasses methods for preventing the development of allergy in a patient at risk of sensitization to antigen or allergen due to impaired gastrointestinal digestion and/or intestinal permeability if exposed to such allergen comprising administering an effective amount of mast cell stabilizer in free or pharmaceutically acceptable acid addition salt form. The invention therefore provides a vaccine against the development of allergy in patients at risk of developing such allergy due to impaired gastrointestinal digestion and/or intestinal permeability. A patient at risk of sensitization to allergen due to impaired gastrointestinal digestion include patients with an impaired acid peptic functions, such as one who has one or more acid peptic diseases.

The term "acid peptic disease(s)" or "acid peptic disorder(s)" refers to any condition associated with impaired gastric acid or pepsin production and/or impaired or insufficient gastric mucosa protection that leads to damages to the gastrointestinal tract. Recent studies showed that impaired gastrointestinal digestion and/or increased intestinal permeability (i.e., gastrointestinal barrier dysfunction)) predispose patients to oral antigen hypersensitivity. Without being bound to any theory, it is believed that impaired gastrointestinal digestion, particularly due to medications or agents that elevate gastric pH prevents efficient gastric degradation of antigen, which in turn leads to hypersensitivity to said antigen/allergen when exposed to it again. Consequently, frequent users of medications that suppress gastric acid secretion or neutralize gastric acid such as proton pump inhibitors, antacids, histamine $H_2$-receptor antagonists, sucrafate and $M_1$ muscarinic receptor antagonists are particularly at risk of sensitization to oral antigen or allergen when exposed to it. In addition, patients having one or more disorders including, but not limited to gastroesophageal reflux disease (GERD), dyspepsia, peptic ulcer (gastric ulcer, duodenal ulcer, esophageal ulcer, stress-related ulcer, alcohol-related ulcer, drug-induced ulcers, e.g., NSAID-related ulcer, acetylsalicylic acid-induced ulcer, e.g., Aspirin-induced ulcer), Zollinger-Ellison syndrome, Barrett's esophagus, gastrinomas, gastritis, preexisting gastrointestinal allergy to an unrelated antigen, preexisting gastrointestinal allergy to one or more antigen(s) or allergen(s), eosinophilic gastritis, eosinophilic enteritis, and eosinophilic esophagitis, are also at risk of sensitization to oral antigen or allergen when exposed to it.

Similarly, patients with increased intestinal permeability or gastrointestinal barrier dysfunction have also shown greater risk of oral sensitization and subsequent development of oral allergy. Patients with barrier dysfunction include patients who suffer from one or more disorders including but not limited to: inflammatory bowel disease (IBD) (e.g., Crohn's disease, coeliac disease, colitis (e.g., ulcerative colitis, collagenous colitis, lymphocytic colitis, ischaemic colitis, diversion colitis, indeterminate colitis)), irritable bowel syndrome (IBS), allergy, gastritis, enteritis, esophagitis, and ulcers (e.g., gastric ulcer, duodenal ulcer, esophageal ulcer or NSAID-related ulcer). Patients with increased intestinal permeability or gastrointestinal barrier dysfunction also include newborns and infants during early months of life where intestinal mucosa is still immature and therefore have incomplete gut integrity which allows for passage of macromolecules and potentially impair physiological establishment of oral tolerance. Other such patients include those with recent heart or liver transplant, particularly those taking tacrolimus, a calcineurin inhibitor, which increases intestinal permeability.

Therefore, in another embodiment, the invention also encompasses methods for preventing the development of an allergy in a patient who regularly experiences one or more symptoms including, but not limited to diarrhea, bloating, loss of appetite, abdominal pain, constipation, nausea, vomiting, dyspepsia, dysphagia, regurgitation and esophageal reflux.

The term "antigen" refers to any substance capable of inducing an immune response. The term "allergen" refers to an antigenic substance which causes an immune response. Allergen(s) as used herein include, but are not limited to a specific allergen protein, mixture of allergen proteins, an extract of the allergen, genetically manufactured allergen, or any combinations thereof. Therefore, the term "food allergen" refers to allergen from food, particularly from eggs, milk, soy, fish, shellfish and various types of fruits, seeds and nuts, most especially from peanuts and tree nuts. Therefore, food allergen(s) include abstract or extract of the food, e.g., eggs, fish, fruits, etc., a specific allergen protein, mixture of allergen proteins, genetically manufactured allergen, or any combinations thereof.

The terms "allergen(s)" and "antigen(s)" may be used interchangeably herein. The present invention encompasses methods for preventing the development of sensitization to antigen(s) or allergen(s).

In another embodiment, the invention encompasses methods for preventing the development of sensitization to new antigen(s) (i.e., substance to which the patient is not yet have an allergic response), particularly oral antigen(s) or allergen(s) (i.e., antigen(s) or allergen(s) that is ingested). Oral antigens and/or allergens include, but are not limited to antigen(s) or allergen(s) found in seafood (e.g., fish, shellfish), tree nuts, hazelnuts, seeds, soy, milk, peach, tomato, banana, strawberries, peanuts, celery, flour, rice, wheat, and eggs. It is believed that patients with impaired gastrointestinal digestion and/or intestinal permeability are likely to develop sensitization to antigen(s) or allergen(s), particularly oral antigen or allergen because of their resistance to alimentary canal digestion or denaturation.

The term "alimentary canal sensitizing allergen(s)" refers to allergen or antigen that is likely to be resistant against gastrointestinal digestion, e.g., allergen with a digestibility of great than 15 as described in Jiang et al., *BMC Bioinformatics* (2007), 8:375, the contents of which are herein incorporated by reference. Antigens or allergens that are particularly resistant to alimentary canal digestion or denaturization include, but are not limited to antigens or allergens in peanuts and hazelnuts.

In one embodiment, the antigen(s) or allergen(s) is ingested either intentionally or unintentionally, e.g., during consumption of food or for purposes of inducing tolerance against the antigen(s) or allergen(s) during immunotherapy or desensitization process. The use of a mast cell stabilizer during desensitization may expedite the process (i.e., RUSH immunotherapy), e.g., by administering higher dosages of the allergen and/or at higher frequency with minimized adverse allergic reaction. For example, a patient undergoing desensitization may begin with RUSH immunotherapy (i.e., expedited desensitization) wherein said patient receives on day one a series of small, escalating doses of allergen in conjunction with (e.g., during, before or after the administration of) the mast cell stabilizer to inhibit or prevent mediator release. Said patient then receives increasing doses of allergen at a slower frequency so as to build-up to a maintenance dose over a period of time. The maintenance dosage and the period of time during which the maintenance doses are administered may vary depending on each patient and said patient's sensitivity to the allergen and may last for years or even indefinitely. By undergoing RUSH immunotherapy with the use of the mast cell stabilizer, however, said patient may be able tolerate larger and/or more frequent doses of allergen with fewer adverse events, thereby, improving patient compliance with the immunotherapy, thereby improving efficacy.

The dose of the antigen or allergen to be administered, and the period of time required to develop tolerance for the antigen or allergen can be determined by one skilled in the art. The antigen or allergen may be administered to the patient through any route known in the art, including, but not limited to oral, inhalation, sublingual, epicutaneous, intranasal, and/or parenteral routes (intravenous, intramuscular, subcutaneously, and intraperitoneal).

Wherein the antigen(s) or allergen(s) is administered to induce tolerance, the mast cell stabilizer may be administered prior to, at the same time or after administration of each dose of allergen. In one embodiment, the mast cell stabilizer is administered prior to the commencement of each dose of allergen(s) or antigen(s). In a particular embodiment, the mast cell stabilizer is administered up to two weeks prior to commencement of each dose of allergen or antigen. In another embodiment, the mast cell stabilizer is administered up to 24 hours prior to each dose of allergen. More preferably, the mast cell stabilizer is administered orally. In an especially preferred embodiment, the mast cell stabilizer is ketotifen fumarate and is administered orally.

The term "mast cell stabilizer" of the invention refers to any compound or agent capable of inhibiting or reducing the release of inflammatory mediators or other autacoids such as histamine, phospholipase $A_2$, platelet-activating factor, metabolites of arachidonic acid, leukotriene $D_4$, and kinins. Examples of mast cell stabilizers include, but are not limited to ketotifen, cromolyn or cromoglycate, nedocromil, bepotastine, ebastine, epinastine, azelastine, lodoxamide tromethamine, lodoxamide trometamol, pemirolast, olopatadine, ketotifen and their derivatives, e.g., ketotifen metabolites, e.g., norketotifen (i.e., 4-(4-piperidinylidene)-4H-benzo[4,5]cyclohepta[1,2-b]thiophen-10(9H)-one), 10-OH-norketotifen, 9-OH-norketotifen, 9,10-di-OH-norketotifen, and those having the general formula:

I)

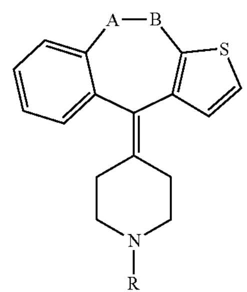

wherein:

a) -A-B- is a moiety having the formula:

i) —CO—$CH_2$— ii) —$CH_2$—CO— iii) —$CH_2$—$CH_2$— iv) —CHOH—$CH_2$— v) —CHOH—CHOH— vi) —$CH_2$—CHOH—; or vii) —CO—CO—; and b) R is a hydroxyalkyl or a carboxyalkyloxyalkyl moiety;

II)

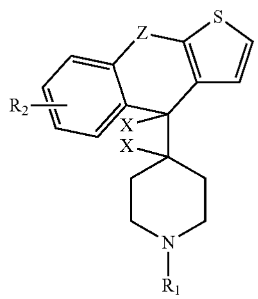

wherein:

a) —Z— is $—CH_2—CH_2—$ or —CH═CH—;

b) $R_1$ is a H or $C_{1-4}$alkyl; and c) $R_2$ is H or halogen.

or III)

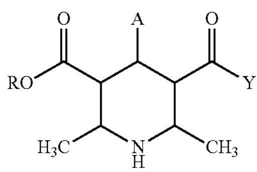

wherein:

a) A is

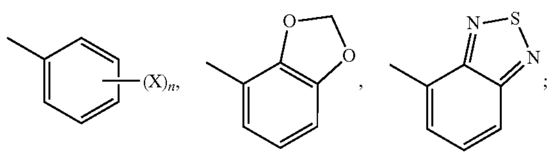

b) n is 1 or 2;

when n is 1, X is H, halogen, $CF_3$, alkyne, $—S(O)_{n'}R$, OR or $NO_2$;

when n is 2, X is H or halogen;

c) n' is 0, 1 or 2;

d) R is $C_{1-5}$(un)branched alkyl;

e) Y is $Z(C(R')(R'))_{n''}Z'$ or

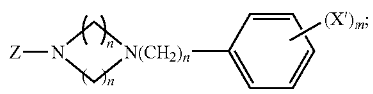

wherein:

i) n" is 2-4;

ii) m is 0, 1, 2, 3;

iii) R' is H or R;

iv) X' is H, halogen, $CF_3$, alkyne, $—S(O)_nR$, OR or $NO_2$;

v) Z is NH or O;

vi) Z' is N(R')(R") or

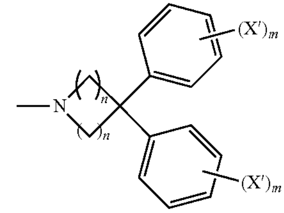

or R" is

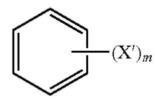

in free or pharmaceutically acceptable salt form, as disclosed in U.S. Pat. Nos. 6,207,683; 6,207,684; 3,491,103; 3,682,930, the contents of each of which are herein incorporated by reference in their entirety. The terms "10-OH-norketotifen", "9-OH-norketotifen" and "9,10-di-OH-norketotifen" refer to norketotifen analogs wherein the hydroxy group(s) is substituted on the $9^{th}$ and/or $10^{th}$ position of the 7-membered ring of norketofen in place of oxo. Preferably, the mast cell stabilizer of the present invention is ketotifen, most preferably, ketotifen fumarate. Mast cell stabilizers as described herein are useful in any of the foregoing methods.

Ketotifen is well known in the art, and may be made via known methods in the art (U.S. Pat. Nos. 3,682,930; 3,272,826, the contents of each of which are hereby incorporate by reference in their entirety) or obtained commercially. Methods for preparing ketotifen derivatives as described above (e.g., norketotifen, 10-OH-norketotifen, etc.) are disclosed in U.S. Pat. Nos. 6,207,683, 6,207,684, 3,491,103, 3,682,930 and Waldvogel et al., *Helv Chem Acta* (1976) 59:866-877, the contents of each of which are herein incorporate by reference in their entirety.

Pharmaceutically acceptable salts of ketotifen may be useful in the present invention, which include, but are not limited to hydrochloride, hydrobromide, hydrogen sulfate, phosphate, nitrate, besylate, maleate and fumarate salts, especially the fumarate.

"An effective amount" refers to any amount that is effective to bring about a desirable effect. Typical dosage of ketotifen is 1-2 mg twice daily for patients 3 years of age or older and 0.05 mg/Kg of body weight twice daily for children under the age of 3 years. Wherein the dosage is non-sedative, the dosage of ketotifen is less than 2 mg, e.g., less than 1 mg, less than 0.75 mg, less than 0.5 mg, twice daily for patients 3 years of age or older. The non-sedative dosage of ketotifen for children under the age of 3 years may be less than 0.05 mg/Kg of body weight twice daily. An effective amount of mast cell stabilizer may vary depending on various factors including but not limited to the patient's bodyweight.

In another embodiment, the invention encompasses a method for prophylactically treating, controlling, delaying or normalizing one or more gastrointestinal disorders administering to a patient in need thereof an effective amount of one or more mast cell stabilizer in free or pharmaceutically acceptable salt form. Recent studies have suggested that gastrointestinal disorders may be independent of the etiology of the diseases, and rather dependent of the alterations of the gastrointestinal barrier and the (in)ability of the body to digest or absorb allergen ingested during the course of food consumption, and moreover that (1) acid release in the stomach may be mediated in part by mast cell activation in the gut, and (2) mast cell activation in the gut may be exacerbated by reduced acid in the stomach, due to reduced degradation of peptides in the stomach. Anyone who suffers from gastrointestinal disorders, particularly due to the digestive system's inability to digest the allergen may be treated with a mast cell stabilizer. Therefore, this method (Method II) is particularly useful for disorders associated with increased intestinal permeability or impaired gastrointestinal digestion, particularly due to medications or agents that elevate gastric pH prevents efficient gastrointestinal degradation of antigen or allergen.

Method II is therefore useful in a patient who suffers from a disorder associated with increased intestinal permeability or impaired gastrointestinal digestion. In particular, Method II is useful in a patient who suffers from a disorder associated with increased intestinal permeability or impaired gastrointestinal digestion and undergoing allergy desensitization.

As used herein, the term "an effective amount" may vary for each patient depending on the severity of the disorder from which the patient suffers and the age and weight of that patient. Wherein the method involves treating gastrointestinal disorders, the effective amount is the amount effective to ameliorate symptoms of the disorder. Wherein the method involves desensitization, an effective amount depends on the sensitivity of the patient to a specific allergen and the amount of allergen administered and the reaction of the patient. Determination of such amount is well within the knowledge of those skilled in the art. Typical dosage of ketotifen is 1-2 mg twice daily for patient three years of age and older and 0.05 mg/Kg of body weight for patient younger than 3 years of age. Ketotifen may also be administered at non-sedative dosages, e.g., less than 1-2 mg, e.g., 0.25 mg, 0.1 mg, twice daily for patient three years of age and older and 0.05 mg/Kg, e.g., 0.025 mg/Kg of body weight for patient younger than 3 years of age.

Unless otherwise noted, dosages of mast cell stabilizers as set forth herein are by weight equivalent to the free base irrespective of whether the drug is administered in salt form or not.

A typical dosage, i.e., of ketotifen may be up to 8 mg twice daily. A typical dosage may include oral administration of 0.5-2 mg twice daily for adults and children 3 years of age and older, e.g. 1 mg b.i.d. A typical dosage for infants and children from 6 months to 3 years of age may be 0.05 mg per kilogram of body weight twice daily, once in the morning and one in the evening. Wherein the mast cell stabilizer, e.g., ketotifen, is administered as a prophylaxis for the prevention of the development of allergy or when ketotifen is enterically coated for local effects rather than systemic effects, the effective amount of mast cell stabilizer, e.g., ketotifen, may be lower than the typical dosage, e.g., such that the dosage is non-sedative, e.g., less than 1 mg b.i.d., preferably less than 0.5 mg b.i.d., when administered to a patient three years of age or older, or less than 0.05 mg per kilogram of body weight, twice daily, e.g., for a patient three years of age or younger.

The mast cell stabilizer, e.g., ketotifen may be administered prior to, at the same time or after administration of each dose of other therapeutic agents, e.g., prior to, up to two weeks prior to or up to 24 hours prior to the administration of other therapeutic agents. With the method of desensitization (administration of allergen in addition to the mast cell stabilizer), said mast cell stabilizer, e.g., ketotifen, may be administered prior to, at the same time or after administration of each dose of allergen. Such mast cell stabilizer may be administered 2 weeks prior to the administration of each dose of allergen. For example, in one embodiment, ketotifen is administered to an adult undergoing allergy desensitization therapy, orally in an amount of 0.75-1.75 mg b.i.d for a period of 1-9 months, e.g., 3 months, from start of desensitization therapy.

The mast cell stabilizers of the invention may be administered via any methods known in the art including, but not limited to oral, parenteral, transmucosal and transdermal administration. The mast cell stabilizers of the invention may also be administered by colonic delivery, e.g., rectal administration. Rectal administration is particularly useful in patients with inflammatory bowel diseases such as Crohn's disease and ulcerative colitis and in diseases such as irritable bowel syndrome.

The antigen(s) or allergen(s) may be administered via any method known in the art, e.g., orally, topically (such as in the form of powders ointments, gels, drops, transdermal patch or transcutaneous patch), via inhalation, sublingually, epicutaneously, intranasally, subcutaneously and parenterally (e.g., intravenous, intramuscular, subcutaneously, and intraperitoneal. In particular embodiment, the antigen(s) or allergen(s) may be administered sublingually, e.g., sublingual oral (SLIT) or sublingual spit (SPIT).

As used herein, the term "anaphylaxis" or "anaphylactic reaction" refers to a Type I hypersensitive reaction, i.e., a rapid-onset hypersensitive IgE-mediated reaction to antigen(s) or allergen(s). The initial manifestation of reaction may range from urticaria (hives), pruritis (itching), allergic rhinitis (hay fever), nausea, vomiting, diarrhea, mild asthma to bronchospasm or mucosal edema as well as hypotension and/or syncope. Symptoms of anaphylaxis in cases of food or hymenoptera allergy are typically manifested relatively quickly, within five to thirty minutes of exposure, rarely more than two hours. Patients at risk of anaphylaxis include those who have been exposed to specific antigen(s) or allergen(s), but did not develop tolerance to it and will likely have a hypersensitive reaction upon re-exposure.

The term "local anaphylaxis" refers to a hypersensitive IgE-mediated reaction to antigen(s) or allergen(s) that results in moderate to severe swelling, redness and/or itching within a limited area of the body, typically near the site of exposure. Typical manifestation of local anaphylaxis includes allergic rhinitis, pruritic, mild asthma and/or urticaria.

The term "systemic anaphylaxis" or "systemic anaphylactic reaction" refers to a systemic hypersensitive reaction to antigen(s) or allergen(s) that results in manifestation of at least one of the symptoms including, but not limited to: difficulty breathing or swallowing as a result of swelling of the tongue, lips and/or oropharynx; wheezing as a result of bronchospasm or mucosal edema; light-headedness; hypotension; syncope; tachycardia; shock; and/or cardiac arrest.

Patients who have had one serious reaction involving the airway, cardiovascular or digestive systems upon initial exposure to antigen(s) or allergen(s) such as food allergen (e.g. shellfish, peanuts, tree nuts, eggs, poppy seeds, or their components, especially peanut and other tree nut allergen) and those who have such history in addition to a family history of anaphylaxis, especially children may particularly benefit from the methods of the invention. Therefore, the methods of the present invention encompass patients who not only have impaired gastrointestinal digestive systems and/or increased intestinal permeability, but also have (1) a personal history of at least one anaphylactic reaction; and/or (2) a personal history of food allergy and a family history of anaphylaxis.

In addition, patients that are particularly vulnerable to systemic anaphylaxis also include those who regularly use β-blockers (e.g. Propanolol). Studies have shown that β-blockers competitively inhibit catecholamine (epinephrine) from binding to β-adrenergic receptor cites. Because catecholamine (epinephrine) induces smooth muscle relaxation and bronchodilation by stimulation of β-receptors, competitive binding of β-blockers to β-receptor cites therefore tends to reduce the effectiveness of epinephrine. Since epinephrine is the number one choice of emergency treatment of anaphylaxis, patients who are regular users of β-blockers are therefore particularly vulnerable as a result of epinephrine resistance.

Patients who are "regular users of β-blockers" herein refer to individuals who take either selective or non-selective β-adrenergic antagonist agents such as propanolol, on a regular basis. Patients who are "regular users of β-agonists" herein refer to individuals who take $\beta_2$-adrenergic agonist agents such as albuterol, on a regular basis, especially patients who take long acting $\beta_2$-adrenergic agonist agents such as formoterol or sameterol, particularly over a sustained period, e.g., at least four weeks.

Patients having a "B16-Arg/Arg genotype" (also refer to as B16-Arg/Arg patient) herein refer to individuals who have homozygous alleles encoding arginine (Arg) at the 16 position of $\beta_2$-adrenergic receptors. These patients appear to be particularly susceptible to deterioration in pulmonary function as a result of regular use of $\beta_2$-adrenergic agents. See, Israel, et al., Am J Respir Crit Care Med Vol 162. pp 75-80 (2000). Genomic DNA may be prepared for genotopic analysis by standard techniques. See Maniatis, et al., Molecular Cloning: A Laboratory Manual. Cold Spring Harbor Laboratory, New York (1989). Analysis of B16 genotype may be done, e.g., by amplification refractory mutation system (ARMS).

Therefore, patients who are resistant to or has diminished or inadequate response to $\beta_2$-adrenergic agonists and/or epinephrine due to regular use of long acting beta-agonists and $\beta_2$-adrenergic antagonist are likely to benefit from the methods of the present invention. Similarly, Patients having a "B16-Arg/Arg genotype" may also benefit from the method of the present invention. Consequently, the methods of the invention, Method I, e.g., any of methods 1.1-1.64, or Method II, e.g., any of methods 2.1-2.22, encompass patients who, in addition to having impaired gastrointestinal digestion and/or increased intestinal permeability issues, are resistant to or have diminished or inadequate response to $\beta_2$-adrenergic agonists and/or epinephrine and/or have a "B16-Arg/Arg genotype".

The phrase "epinephrine resistance" refers to patients who exhibit deterioration in pulmonary function as a result of regular use of either β-blockers or β-agonists.

The mast cell stabilizers may be administered alone, in conjunction or simultaneously with other therapeutic agents. The term "in conjunction with" may include administering an agent such as a mast cell stabilizer e.g., ketotifen, concomitantly, e.g., as an admixture; separately but simultaneously or concurrently; or sequentially with an allergen or with other therapeutic agents. These therapeutic agents include but are not limited to NSAID, ASA drugs, histamine-1 receptor antagonists, histamine-2 receptor antagonists, corticosteroids, PDE IV inhibitors, beta-adrenergic agonists, anticholinergic agents, epinephrine and IgE antagonists (including variant anti-IgE antibodies (non-human mammalian, chimeric, polyclonal and/or monoclonal antibodies (Mabs) and fragments thereof (e.g., proteolytic digestion or fusion protein products) and nucleotides or polypeptides encoding or containing IgE sequences or nucleotides or polypeptides that induce anti-IgE antibody production (e.g., anti-IgE immunogenic polypeptide as disclosed in U.S. Pat. No. 6,913,749, U.S. Pat. App. No. 2004/0076625A1 and 2003/0031663A1), especially IgE antagonist and polypeptides capable of differential binding to Fc.epsilon.RI and Fc.epsilon.RII.); antagonist of cytokines, such as, for example, monoclonal antibody to TNF-alpha, soluble TNF-alpha receptor-Fc fusion protein, and/or IL-1 receptor; kinase inhibitors, e.g., inhibitors of spleen tyrosine kinase (syk), and inhibitors of kinase-activated pathways, e.g. inhibitors of STAT proteins. In a preferred embodiment, the mast cell stabilizers, e.g., ketotifen is administered in conjunction with an NSAID, ASA drug, antacid or a proton pump inhibitor.

The term "gastrointestinal disorders" refers to any disorder associated with increased intestinal permeability or impaired gastrointestinal digestion. Disorders associated with increased intestinal permeability include but are not limited to selected from one or more of the following: inflammatory bowel disease (IBD) (e.g., Crohn's disease, coeliac disease, colitis (e.g., ulcerative colitis, collagenous colitis, lymphocytic colitis, ischaemic colitis, diversion colitis, indeterminate colitis)), irritable bowel syndrome (IBS), allergy, gastritis, enteritis, esophagitis, and ulcers (e.g., gastric ulcer, duodenal ulcer, esophageal ulcer or NSAID-related ulcer). Disorders associated with impaired gastrointestinal digestion include, but are not limited to acid peptic diseases. Therefore, disorders associated with impaired gastrointestinal digestion include, but are not limited to gastroesophageal reflux disease (GERD), dyspepsia, peptic ulcer (gastric ulcer, duodenal ulcer, esophageal ulcer, stress-related ulcer, alcohol-related ulcer, drug-induced ulcers, e.g., NSAID-related ulcer, acetylsalicylic acid-induced ulcer, e.g., Aspirin-induced ulcer), Zollinger-Ellison syndrome, Barrett's esophagus, gastrinomas, gastritis, eosinophilic gastritis, eosophillic gastroenteritis, preexisting gastrointestinal allergy to one or more antigen(s) or allergen(s), eosinophilic enteritis, and eosinophilic esophagitis. In a preferred embodiment, disorder of Method II is GERD.

In other cases, disorders include NSAID-induced or ASA-induced, e.g., Aspirin-induced, gastrointestinal disorders including but not limited to dyspepsia, GERD, bloating, belching, nausea.

The term "enteric coat" or "enteric coating" or "enterically coated" refers to any coating that is preferably resistant to acid digestion. Therefore, enterically coated mast cell stabilizer, e.g., ketotifen, allows administration of such agent in a low dose for a local, non-systemic effect, thereby allowing the dosage to be non-sedative.

The term "intestinal permeability" refers to mucosal capacity which allows molecules to pass from the intestinal lumen to the blood stream. The term "increased intestinal permeability" refers to a situation wherein the intestinal permeability in a patient is altered, e.g., higher, than healthy control. Patients with increased intestinal permeability include but are not limited to patients with inflammatory bowel disease (IBD) (e.g., Crohn's disease, coeliac disease, colitis (e.g., ulcerative colitis, collagenous colitis, lymphocytic colitis, ischaemic colitis, diversion colitis, indeterminate colitis)), irritable bowel syndrome (IBS), allergy, gastritis, enteritis, esophagitis, and ulcers (e.g., gastric ulcer, duodenal ulcer, esophageal ulcer, stress-related ulcer, alcohol-related ulcer, drug-induced ulcers, e.g., NSAID-related ulcer, acetylsalicylic acid-induced ulcer, e.g., Aspirin-induced ulcer). Patients with increased intestinal permeability or gastrointestinal barrier dysfunction also include newborns and infants during early months of life where intestinal mucosa is still immature and therefore have incomplete gut integrity which allows for passage of macromolecules and potentially impair physiological establishment of oral tolerance. Other such patients include those with recent heart or liver transplant, particularly those taking tacrolimus, a calcineurin inhibitor, which increases intestinal permeability.

In one example, ketotifen or other mast cell stabilizers may be administered in the form of a viscous gel for sustained release, in order to prevent or alleviate or to treat gastrointestinal and esophageal inflammation, and thus minimize signs and symptoms of inflammation or to repair tissue. Remington, *The Science and Practice of Pharmacy,* $21^{st}$ edition, describes examples of gels that may be used. For example, gelling agents used to form gels may be in a concentration of less than 10% and often are in 0.5 to 2.0% range. Gelling agents that may be used to gel ketotifen or an equivalent may include acacia, alginic acid, bentonite, carbomer, carboxymethylcellulose sodium, cetostearyl alcohol, colloidal silicon dioxide, ethylcellulose, gelatin, guar gum, hydroxyethylcellulose, hydroxypropyl cellulose, hydroxypropyl methylcellulose, magnesium aluminum silicate, maltodextrin, methylcellulose, polyvinyl alcohol, povidone, propylene carbonate, propylene glycol alginate, sodium aliginate, sodium starch glycolate, starch, tragacanth, and xanthan gum. Other gelling agents may also be used.

In one example, alginic acid may be used as a gelling agent and used in concentrations between 1% and 5% as a thickening agent. Salts such as calcium salts may result in substantially higher viscosity. In another example, carbomer resins may be used to provide sustained release properties in both the stomach and intestinal tract. Alcohol may be added to carbomer gels to decrease their viscosity. A neutralizer may be added to thicken the gel after the carbomer is dispersed. For example, sodium hydroxide or potassium hydroxide may be used in carbomer dispersions containing less than 20% alcohol. Triethanolamine may be used to neutralize carbomer resins containing up to 50% ethanol.

In another example, carboxymethylcellulose may be used to produce gels in concentrations of 4% to 6% of medium viscosity grade. Glycerin may be added to prevent drying. In another example, tragacanth gum may be used to prepare gels that are stable at a pH range of 4-8, and such gels should be preserved or sterilized by autoclaving. Aqueous dispersions are prepared by adding tragacanth powder to rapidly mixed water, thus preventing lumping of tragacanth gum in water. Lumps may also be prevented by wetting the tragacanth gum with ethanol, glycerin, or propylene glycol.

In another example, gelatin gels using ketotifen may be prepared by dispersing gelatin in hot water followed by cooling. Alternatively, gelatin may be wetted with an organic liquid such as ethyl alcohol or propylene glycol, followed by the addition of hot water and cooling. Magnesium aluminum silicate forms thixotropic gels at concentrations of about 10%.

In another example, methylcellulose may be used to form gels at concentrations up to about 5%. This powder is dispersed with high shear at 80-90 degrees Celsius in a portion of water to allow for faster hydrating in hot water. Once methylcellulose powder is finely dispersed, water is added with moderate stirring. Alcohol or propylene glycol is often used to help wet the powders. In yet another example, poloxamer gels made from selected forms of polyoxyethylene-polyoxypropylene copolymers in concentrations ranging from 15% to 50%. Polyvinyl alcohol may be used at concentrations of about 2.5% in the preparation of various jellies.

In another example, high molecular weight forms of povidone may be used to prepare gels in concentrations up to about 10%. Povidone's advantages include being compatible with a wide range of inorganic salts, natural and synthetic resins, and other chemicals.

Gels using any of the above reference compounds may be used to gel ketotifen or an equivalent in the form of single-phase gels, which offer faster release of the drug and is independent of the water solubility of the drug. A single phase gel using ketotifen may use a methylcellulose and carbomer gel base, which may have methylcellulose, 4000 cps (1.0%), carbomer 934 (0.35%), 1 N Sodium Hydroxide solution (qs to pH 7, propylene glycol (16.7%), and methyl paraben (0.015%), for example.

In another example of a single phase gel, sodium alginate may be used. The sodium alginate gel base may include 10 g sodium alginate, 10 g of glycerin, 0.2 methyl hydroxybenzoate, 0.5 g of a soluble calcium salt such as calcium gluconate, and purified water to make 100 ml of a single phase gel solution.

In yet another example, a carbomer gel solution having ketotifen may include 2 g of Carbomer 934, 1.65 ml of triethanolamine, 0.2 g of methyl paraben, 0.05 g of propyl paraben, and purified water to make 100 ml of a single phase gel solution.

The mast cell stabilizer may be prepared in other topical preparations such as a solution, or as a suspension, for example. One example of a solution is a nasal solution designed to be administered to the nasal passage in the form of an emulsion or a suspension, for example. An aqueous nasal solution may be isotonic and may be slightly buffered to maintain a pH of 5.5 to 6.5.

The mast cell stabilizer may be prepared in the form of a syrup, a concentrated, viscous aqueous solution of sugar or a sugar substitute with or without flavors and medical substances. Syrups may be used to apply sugar coatings to tablets, particularly those with disagreeable aromas or acrid taste. Polyols such as glycerin or sorbitol may be added to retard crystallization of sucrose or to increase the solubility of added ingredients.

The mast cell stabilizer may be prepared as a suspension. A suspension may be defined as a two-phase system of an undissolved or immiscible material dispersed in a vehicle such as a liquid, solid or a gas. One example includes a sustained release suspension. Durect utilizes the SABER system for sustained release suspensions, which uses a non-polymeric, non-water soluble high viscosity liquid carrier material such as sucrose acetate isobutyrate to provide controlled release of active ingredients. The mast cell stabilizer may be mixed with a small amount of a pharmaceutically acceptable solvent to form a low viscosity solution or suspension, which is then mixed with a high viscosity carrier. This suspension may be administered via injection, orally, or as an aerosol, forming an adhesive, biodegradable depot upon contact with tissues.

The mast cell stabilizer may also be prepared as a lotion or an ointment. Lotions generally are liquid or semi-liquid preparations that contain one or more active ingredients in an appropriate vehicle and are often suspensions of solids in an aqueous medium. Ointments are semisolid preparations for external application to the body.

In yet another example, the mast cell stabilizer may be prepared in the form of a bioadhesive delivery system. In one example, a gel may contain a bioadhesive polymer. For example, polycarbophil and other polyacrylic acid-based polymers may chelate calcium ions, and may allow for increase in cellular transport, by opening tight junctions, which are calcium-dependent. Matrices containing polyacrylates, cellulose derivatives, or chitosans may be chemically modified and improve certain properties of these matrices.

The mast cell stabilizer may be administered orally, for example, in the form of a dissolving wafer, a dissolving tablet, a lozenge, or a lollipop, for example.

Other examples of topical preparations using the mast cell stabilizer are known in the art, and thus the mast cell stabilizer may be readily formulated for such use. Other examples of oral delivery are also known in the art.

Drug delivery systems are known in the art. Drug delivery systems may include liposomal carrier vehicles to deliver a mast cell stabilizer, for example.

The methods and compositions may be used to prevent, alleviate, or treat any disease having gastrointestinal and esophageal inflammation. Examples of such diseases included acid-related disorders such as gastro esophageal reflux diseases, eosinophilic esophagitis, peptic ulcer disease and gastrointestinal inflammatory conditions such as Helicobacter pylori gastritis, for example. Diseases such as dysphagia are also contemplated within the scope of treatment.

EXAMPLES

The matters set here are offered by way of illustration only and not as limitations. While particular embodiments have been shown and described, it will be apparent to those skilled in the art that changes and modifications may be made without departing from the broader aspects of invention.

Example 1

Use of Ketotifen as a Prophylaxis in Patients at Risk of Sensitization to Hazelnut Allergen Twenty-four patients with adverse food reaction are included in this study. As controls, twelve patients matched for age and gender and a history of GERD (Group A) and another twelve patients matched for age and gender and no history of any gastrointestinal disorder (Group B) are included. The history of use of antacids and satisfaction are recorded for both groups.

To analyze hypersensitivity to hazelnut, a double-blind, randomized, dose-ranging study is carried out with patients with a history of hazelnut allergy manifested by urticaria, angioedema, respiratory tract symptoms or hypotension generally using the methods described in Israel et al., Am. J. Respir. Crit. Care Med., (2000) 164:75-80. Eligible patients include those with serum total IgE level of 30-1000 IU/mL and/or a positive skin-prick test to hazelnut. Patients must have asthma condition under control with a forced expiratory volume in one second that is at least 80 percent of the predicted value. Patients may not take systemic corticosteroids, beta-blockers, acetylcholinesterase, antihistamines and anti-depressants during the study.

Before enrollment, threshold level for reactivity to hazelnut allergen is confirmed by a screening double-blind, placebo-controlled oral food challenge. Base line spirometry, peak expiratory flow rates and continuous cardiac monitoring is established. Vital signs are checked, chest auscultation is performed, and peak expiratory flow rates are monitored every 30 minutes during the food challenge and for at least 2 hours after the last dose or the abatement of any symptoms or signs. Patients are given an initial dosage of 1 mg of hazelnut followed successively by 5, 10, 20, 50, 100, 200, 500, 1000 and 2000 mg of hazelnut flour or matching placebo capsules every 40 minutes until a definite reaction is occurring, such as manifestation of nausea, abdominal pain, vomiting, throat tightness, chest tightness, wheezing, persistent cough, rhinitis, conjunctivitis, pruritus, hives, and angioedema. To maximize safety and prevent severe reactions, the end point for the oral food challenge is the threshold dose for an allergic reaction.

Peak expiratory flow rates are monitored every 30 minutes during food challenge for at least 2 hours after the last does or abatement of any symptoms or signs. A tolerance of 2000 mg of hazelnut flour is considered to have a negative allergy test result. If patients manifest clear signs of hypersensitivity reaction, the patient is then given activated charcoal slurry (Liqui-Char, Jones Pharma) to adsorb residual hazelnut protein in the stomach. Each patient qualified to enter the study is required to have one positive and one negative result to hazelnut at screening.

Hazelnut flour is made by grinding hazelnuts. The hazelnuts are defatted, and then various doses (1 mg to 2 g) are loaded into gel capsules. Matching placebo capsules are filled with similar amounts of cornstarch. For masking purposes, the capsules are rolled in tuna oil before hazelnut capsules, placebo and Ketotifen tablet are administered orally.

Six patients from Group A are administered an oral dose of 0.5 (2 patients), 1 (2 patients), or 2 mg (2 patients) of ketotifen orally twice daily (Group A-1) and another five patients from Group A are administered an oral dose of placebo (Group A-2) twice daily, once in the morning and once in the evening during the test period. Six patients from Group B are administered an oral dose of 0.5 (2 patients), 1 (2 patients), or 2 mg (2 patients) of ketotifen orally twice daily (Group B-1) and another six patients from Group A are administered an oral dose of placebo (Group B-2) twice daily, once in the morning and once in the evening during the test period. Patients then undergo an oral food challenge with hazelnut flour at two, four and six weeks. The oral food challenge with hazelnut flour alone is initiated at 1 mg or 100 mg, depending on the threshold determined during the screening study, and is then escalated in accordance with the above schedule to 4000 mg and then 8000 mg if tolerated. Each dose level is to be completed before enrollment at the next level. Every two weeks, blood and urine samples are obtained. Total hazelnut-specific IgE level is measured by fluorescence enzyme immunoassay (CAP-System, FEIA).

The result will show Group A-1 and B-1 are observed to have significant increased tolerance, e.g., reduced severity reaction, to hazelnut upon oral ingestion compared to group A-2 and B-2 respectively. The result will also show that Group A-1 and A-2 are observed to have reduced severity of allergic reaction to hazelnut compared to Group B-1 and B-2 respectively. The results further show that patients in Group A1 reported low satisfaction with symptom relief from antacids use pre-study. Reflux symptom reporting by Groups A1 during the study are significantly lower than those reported by Group A2.

Example 2

Use of Ketotifen During Desensitization to Airborne Allergen

To evaluate the effectiveness of mast cell stabilizer, e.g., ketotifen, in desensitization or immunotherapy, particularly RUSH immunotherapy, a randomized, double-blind, placebo-controlled study is performed. Patients are randomly assigned to 4 treatment groups (1:1:1:1). Pretreatment with either ketotifen, 1 mg, b.i.d., or placebo, is carried out for nine weeks to protect, prevent, inhibit or ameliorate allergic reaction, particularly to prevent, normalize or ameliorate gastrointestinal symptoms. One-day rush immunotherapy (week 0) is completed at least 3 weeks before the start of the ragweed season. On the day of rush immunotherapy, the patients receive 6 injections of either placebo or aqueous short ragweed extract. Ragweed dosing starts with a diluted extract containing 0.012 μg of Amb a 1 (a major allergen in ragweed) over a 3-hour period, reaching a maximum of 1.2 μg of Amb a 1. Some subjects also receive 2 additional injection of ragweed extract, with a maximum of 4 μg dosage over a 5 hour period. Each week during the immunotherapy period, the patients receive increasing doses of short ragweed extract (2, 4, 6, and 8 μg Amb a 1) followed by 8 weekly maintenance injection of 12 μg Amb a 1, for a total of 12 weeks.

The efficacy end point is determined by comparing the average daily allergy severity scores (measured on a scale of 0-3) between patients receiving ketotifen plus immunotherapy versus those who receive just immunotherapy alone. The score is calculated from the average of individual scores for symptoms of gastrointestinal disorders, e.g., abdominal pain, nausea, diarrhea, and/or heartburn.

The result will show that patients who receive ketotifen plus immunotherapy have fewer adverse events of gastrointestinal disorders and significantly improved allergy severity scores compared to those receiving immunotherapy alone.

Example 3

Use of Ketotifen During Desensitization to Oral Allergen

To evaluate the efficacy of ketotifen in desensitization process against oral allergen such as hazelnut, a similar study as described in Example 3 may be carried out except with the use of hazelnut extract rather than ragweed extract. The studies will show that patients who receive ketotifen plus immunotherapy have fewer adverse events of gastrointestinal disorders and significantly improved allergy severity scores compared to those receiving immunotherapy alone.

Example 4

Use of Ketotifen for the Treatment of Gastrointestinal Disorders and Prophylaxis of the Development of Sensitivity to Allergen The following study may be carried out to analyze the effectiveness of mast cell stabilizer in treating gastrointestinal disorders and/or as a prophylaxis against the development of allergy in patients at risk of developing sensitivity to such allergen, e.g., sensitivity to hazelnut, when exposed to it.

Sera of nine adult patients who have a history of GERD are collected. None of the patients report adverse reactions to inhalant or food allergens; however, IgE immunoblots are performed to screen their allergic state. Three patients from Group A are administered a proton pump inhibitor, e.g, omeprazole (Group A-1). Three patients from Group A are administered an oral dose of 0.5, 1, or 2 mg of ketotifen orally twice daily (Group A-2). Three patients from Group A are administered an oral dose of ketotifen as in Group A-2, plus a proton pump inhibitor, e.g, omeprazole, 1×20 mg/d (Group A-3).

Serum IgE and Skin Tests in Patients: Sera are tested for allergen-specific IgE against hazelnut and inhalative allergens from tree pollen (eg, birch, hazel, and alder), grass pollen, weed pollen, molds, house dust mites, insect venoms, and animal dander. Immunoblot testing is performed before and 3 and 8 mo after the onset of the treatment omeprazole, omeprazole plus ketotifen or ketotifen only. This system allows the detection of IgE by color reactions through formation of precipitates on nitrocellulose test strips. The coloration is directly proportional to the specific antibody content of the serum sample. Evaluation is carried out after complete drying with a CCDcamera, which assigns the results to the test classes of absolute IgE amounts. Results are considered positive at a class of ≥2 (≥0.75 kU/L). Additionally, total IgE is determined before and at the 3-mo time point. Patients with hazelnut-specific IgE in their sera are further subjected to skin tests with hazelnut extract at the 8-mo time point.

Gastrointestinal Symptoms: Symptoms of gastrointestinal side effects such as GERD, nausea, abdominal pain, vomiting, gastritis and/or dyspepsia are recorded based on the severity and frequency of the symptoms.

Oral Provocation of Patients: Single-blind, placebo-controlled oral provocation with hazelnut is performed 11-13 mo after the onset of therapy in the patients with hazelnut-specific IgE. Patients are tested with hazelnut (doses of 0.15, 0.6, 3.0, 15.0, and 60.0 mg/caps). The different doses were given at an interval of 60 min. The tests are stopped at the first appearance of symptoms.

Western Blotting and Dot Blots: Hazelnut extract (2 mg/mL) is separated under reducing conditions in a 12% SDS-PAGE and electroblotte onto a nitrocellulose membrane. One blot strip is blocked with PBS and 0.5% Tween, and staining is performed with commercially available black ink in PBS and 0.05% Tween (1:1000) to control the blotted protein. Remaining blot strips are blocked with buffer (50 mmol/L sodium phosphate buffer, pH 7.5; 0.5% Tween 20, 0.5% bovine serum albumin); incubated with human sera (1:10) overnight at 4° C.; washed, and incubated with $^{125}$I-labeled antihuman IgE (1:20) overnight. The reaction is visualized by exposing blots to BIOMAX-MS films. For dot blots, 1 μg/dot of recombinant Bet v 1, Cor a 1, or Art v 1 or 2 μg/dot of hazelnut extract is applied onto nitrocellulose, blocked, and incubated as above with sera from the 5 hazelnut allergic patients in the omeprazole group.

The result will show that patients receiving proton pump inhibitor omeprazole only (Group A-1) are observed to have improved GERD symptoms, but blood sera show hazelnut-specific IgE after onset of treatment, while patients receiving ketotifen only (Group A-2) are observed to have improved GERD symptoms and hazelnut-specific IgE. The study also will also show that patients treated with omeprazole and ketotifen (Group A-3) are observed to have improved GERD symptoms and decreased hazelnut-specific and other allergen specific IgE.

Example 5

Use of Ketotifen for Treatment of Gastrointestinal Disorders

To evaluate the effectiveness of ketotifen in patients who have a history of GERD, but are unresponsive to conventional proton pump inhibitors or antacids, two groups of patients are tested as similar to Example 4. One group is administered ketotifen at 0.5 mg, 1 mg, 2 mg, twice daily. The second group is treated with omeprazole, 1×20 mg/d. Sera IgE are evaluated before and after administration of ketotifen or omeprazole and gastrointestinal symptoms are recorded based on severity and frequency of symptoms. The study will show that patients administered with ketotifen alone will have improved GERD symptoms and few new allergen specific IgE in blood sera while patients administered omeprazole have no improvements or more severe GERD symptoms and new or increased levels of allergen-specific IgE in their blood sera.

Example 6

Inhibition of Sensitization to New Allergen in a Model of Pre-Existing Food Allergy A study is conducted to determine whether atopic animals are more easily sensitized to a newly introduced allergen (e.g., hazel nut). Four groups of female BALB/c mice (7-8 weeks old) are sensitized by intraperitoneal (IP) injections 2 weeks apart with ovalbumin (OVA; 50 μg) in 1.3% aluminum hydroxide (200 μl) followed 2 weeks later by 7 seven intragastric challenges (every other day) with saline or 5, 10, or 50 mg OVA, a selected dose of hazel nut, or combination of OVA and hazelnut. Endpoints include observance of diarrhea after intragastric challenge, Serum total and antigen specific IgE and IgG 1, gut to body weight ratio, intestinal permeability, and histological evaluation are performed. Results demonstrate that an existing gastrointestinal phenotype enhances the sensitization to a new orally administered food allergen. A second experiment assesses the ability of ketotifen to inhibit the induction of allergy to a newly introduced food allergen in animals with a pre-existing gastrointestinal allergy. Ketotifen significantly suppresses the gastrointestinal allergy phenotype in female BALB/c mice sensitized OVA upon OVA intragastric challenge. Also, OVA sensitized BALB/c mice receiving intragastric hazelnut with ketotifen or OVA plus hazelnut with ketotifen fail to develop new sensitivity to hazel nut as assessed by the criteria detailed above. A group of BALB/c mice similarly sensitized to OVA, but continuing to receive intragastric hazel nut in the absence of intragastric OVA fails to develop an observable gastrointestinal allergy phenotype.

Example 7

Treatment of Eosinophilic Esophagitis with Sustained Topical Delivery of Ketotifen To evaluate the effectiveness of ketotifen in patients who have a diagnosis of eosinophilic esophagitis and food allergy, two groups of patients will be tested. One group is orally administered ketotifen at 0.5 mg, 1 mg, or 2 mg, twice daily as a tablet. The second group is treated with a topical gel that provides esophageal topical ketotifen concentrations equal to or greater than 10 to minus 4 molar for a sustained period of time without increasing systemic concentrations beyond concentrations normally seen with oral administration of comparable doses by oral tablets. Patients receiving ketotifen by oral tablet also report partial improvement of symptoms. Blood analysis demonstrates decreased eosinophilia and esophageal biopsies reveals fewer numbers of eosinophils and mast cells and less degranulation compared to biopsies that are taken pre-treatment; however, the results are inferior to those observed with the topical gel formulation which approaches the effectiveness of topical corticosteroids. Biopsy results suggest that tissue remodeling and fibrosis are ameliorated by topical esophageal delivery of ketotifen.

Alternative combinations and variations of the examples provided will become apparent based on this disclosure. It is not possible to provide specific examples for all of the many possible combinations and variations of the embodiments described, but such combinations and variations may be claims that eventually issue.

What is claimed is:

1. A method for the prophylaxis of the development of a peanut or hazelnut allergy in a patient undergoing allergy desensitization and wherein the patient is at risk of sensitization to one or more antigen(s) or allergen(s) if said patient is exposed to said antigen(s) or allergen(s), and wherein said risk of sensitization is due to existing impaired gastrointestinal digestion and/or increased intestinal permeability, wherein said method comprises administering an effective amount of a mast cell stabilizer, wherein the mast cell stabilizer is ketotifen, in free or pharmaceutically acceptable salt form; and wherein the antigen(s) or allergen(s) are administered and are peanuts or hazelnuts.

2. The method according to claim 1, wherein said patient suffers from one or more of the following: inflammatory bowel disease, irritable bowel syndrome (IBS), preexisiting gastrointestinal allergy, gastritis, enteritis, esophagitis and ulcers.

3. The method according to claim 1, wherein said patient suffers from impaired gastrointestinal digestion.

4. The method according claim 1, wherein said patient suffers from one or more disorders selected from the following: gastroesophageal reflux disease, dyspepsia, peptic ulcer, Zollinger-Ellison syndrome, Barrett's esophagus, gastrinomas, gastritis, eosinophilic gastritis, eosinophillic gastroenteritis, eosinophilic enteritis, and eosinophilic esophagitis.

5. The method according to claim 1, wherein ketotifen is administered prior to the commencement of each dose of allergen.

6. The method according to claim 1, wherein ketotifen is administered up to two weeks prior to commencement of each dose of allergen.

7. The method according to claim 1, wherein the patient receives an oral dose of 0.5, 1 or 2 mg ketotifen twice daily.

8. The method according to claim 1, said ketotifen is administered in conjunction with one or more agents selected from a group consisting of proton pump inhibitors, antacids, histamine $H_2$-receptor antagonists, sucralfate, and $M_1$ muscarinic receptor antagonists, in free or pharmaceutically acceptable salt form.

9. The method according to claim 8, wherein said agent is a proton pump inhibitor in free or pharmaceutically acceptable salt form.

10. The method according to claim 8, wherein said agent is an antacid.

11. The method according to claim 8, wherein said agent is a histamine $H_2$-receptor antagonist in free or pharmaceutically acceptable salt form.

12. The method according to claim 1, wherein said ketotifen is ketotifen fumarate in free or pharmaceutically acceptable salt form.

* * * * *